(12) United States Patent
Oster

(10) Patent No.: US 10,010,425 B2
(45) Date of Patent: *Jul. 3, 2018

(54) PROSTHESIS

(71) Applicant: Swemac Innovation AB, Linkoping (SE)

(72) Inventor: Lars Oster, Lidkoping (SE)

(73) Assignee: SWEMAC INNOVATION AB (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/235,219

(22) Filed: Aug. 12, 2016

(65) Prior Publication Data

US 2016/0374817 A1 Dec. 29, 2016

Related U.S. Application Data

(62) Division of application No. 13/984,111, filed as application No. PCT/SE2011/051594 on Dec. 27, 2011, now Pat. No. 9,445,912.

(30) Foreign Application Priority Data

Mar. 4, 2011 (SE) ...................................... 1150197

(51) Int. Cl.
  *A61F 2/42* (2006.01)
  *A61B 17/72* (2006.01)
  (Continued)

(52) U.S. Cl.
  CPC ........ *A61F 2/4241* (2013.01); *A61B 17/1739* (2013.01); *A61B 17/7291* (2013.01);
  (Continued)

(58) Field of Classification Search
  CPC ........... A61F 2/4261; A61F 2002/4264; A61B 17/7291
  See application file for complete search history.

(56) References Cited

U.S. PATENT DOCUMENTS 4,115,875 A 9/1978 Rambert et al.
4,304,011 A 12/1981 Whelan, III
(Continued)

FOREIGN PATENT DOCUMENTS

DE 3347055 7/1985
FR 2692778 12/1993
(Continued)

*Primary Examiner* — David H Willse
*Assistant Examiner* — Javier Blanco
(74) *Attorney, Agent, or Firm* — Tarolli, Sundheim, Covell & Tummino LLP

(57) ABSTRACT

A prosthesis for primary artrodhesis can be used for artroplasty and a prosthesis for artroplasty comprises members for artrodhesis. The prosthesis (1b) for primary artrodhesis comprises a locking member (33b) with an attachment portion (16b) which is insertable into a hole (8b) in a first attachment member (4b) of the prosthesis for location of the locking member therein, and a lockable member (34b) integral with a second attachment member (5b) of the prosthesis. The lockable member (34b) is configured for adjustable setting thereof relative to the locking member (33b) and for fixation thereof, in set position, to the locking member. Alternatively, the lockable member comprises an attachment portion which is insertable into a hole in the second attachment member for location of the lockable member therein. At the prosthesis for artroplasty, the hole in the first screw-like attachment member is partly configured to define a press fit with an attachment pin of a socket member and partly threaded to permit, after removal of the socket member, during artrodhesis, securing by screwing in the hole of the locking member for cooperation with a lockable member which is configured for adjustable setting thereof relative to the locking member and for fixation thereof, in set position, to the locking member.

4 Claims, 20 Drawing Sheets

(51) Int. Cl.
 *A61F 2/30*     (2006.01)
 *A61F 2/46*     (2006.01)
 *A61B 17/17*    (2006.01)
 *A61B 17/80*    (2006.01)

(52) U.S. Cl.
 CPC ........ *A61B 17/8061* (2013.01); *A61F 2/4261* (2013.01); *A61B 17/1725* (2013.01); *A61B 17/1782* (2016.11); *A61B 17/80* (2013.01); *A61F 2002/3085* (2013.01); *A61F 2002/30332* (2013.01); *A61F 2002/30405* (2013.01); *A61F 2002/30433* (2013.01); *A61F 2002/30471* (2013.01); *A61F 2002/30494* (2013.01); *A61F 2002/30507* (2013.01); *A61F 2002/30538* (2013.01); *A61F 2002/30578* (2013.01); *A61F 2002/30607* (2013.01); *A61F 2002/30614* (2013.01); *A61F 2002/30622* (2013.01); *A61F 2002/30632* (2013.01); *A61F 2002/30649* (2013.01); *A61F 2002/4256* (2013.01); *A61F 2002/4264* (2013.01); *A61F 2002/4677* (2013.01); *A61F 2220/0016* (2013.01); *A61F 2250/0006* (2013.01)

(56) References Cited

U.S. PATENT DOCUMENTS

| | | |
|---|---|---|
| 5,147,386 A | 9/1992 | Carignan et al. |
| 5,167,661 A | 12/1992 | Wagenknecht |
| 5,405,347 A | 4/1995 | Lee et al. |
| 6,099,571 A | 8/2000 | Knapp |
| 6,475,242 B1 | 11/2002 | Bramlet |
| 7,837,738 B2 | 11/2010 | Reigstad et al. |
| 2004/0153073 A1 | 8/2004 | Orbay |
| 2007/0078519 A1 | 4/2007 | Klotz |
| 2008/0065224 A1 | 3/2008 | Reigstad et al. |
| 2009/0171463 A1 | 7/2009 | Brehm |
| 2010/0130978 A1 | 5/2010 | Orbay et al. |
| 2011/0160728 A1 | 6/2011 | Blitz et al. |

FOREIGN PATENT DOCUMENTS

| | | |
|---|---|---|
| WO | 9104718 | 4/1991 |
| WO | 2010096724 | 8/2010 |

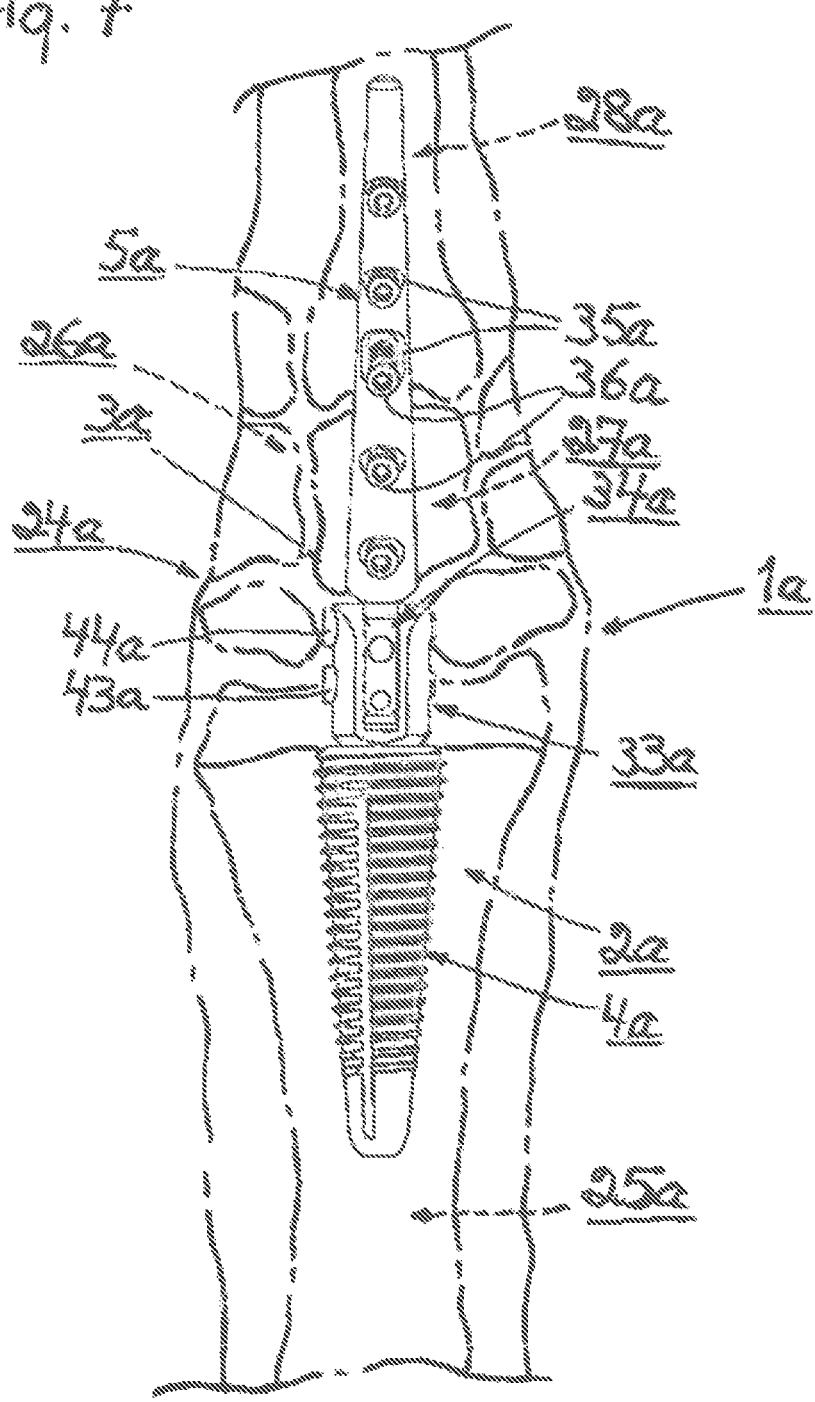

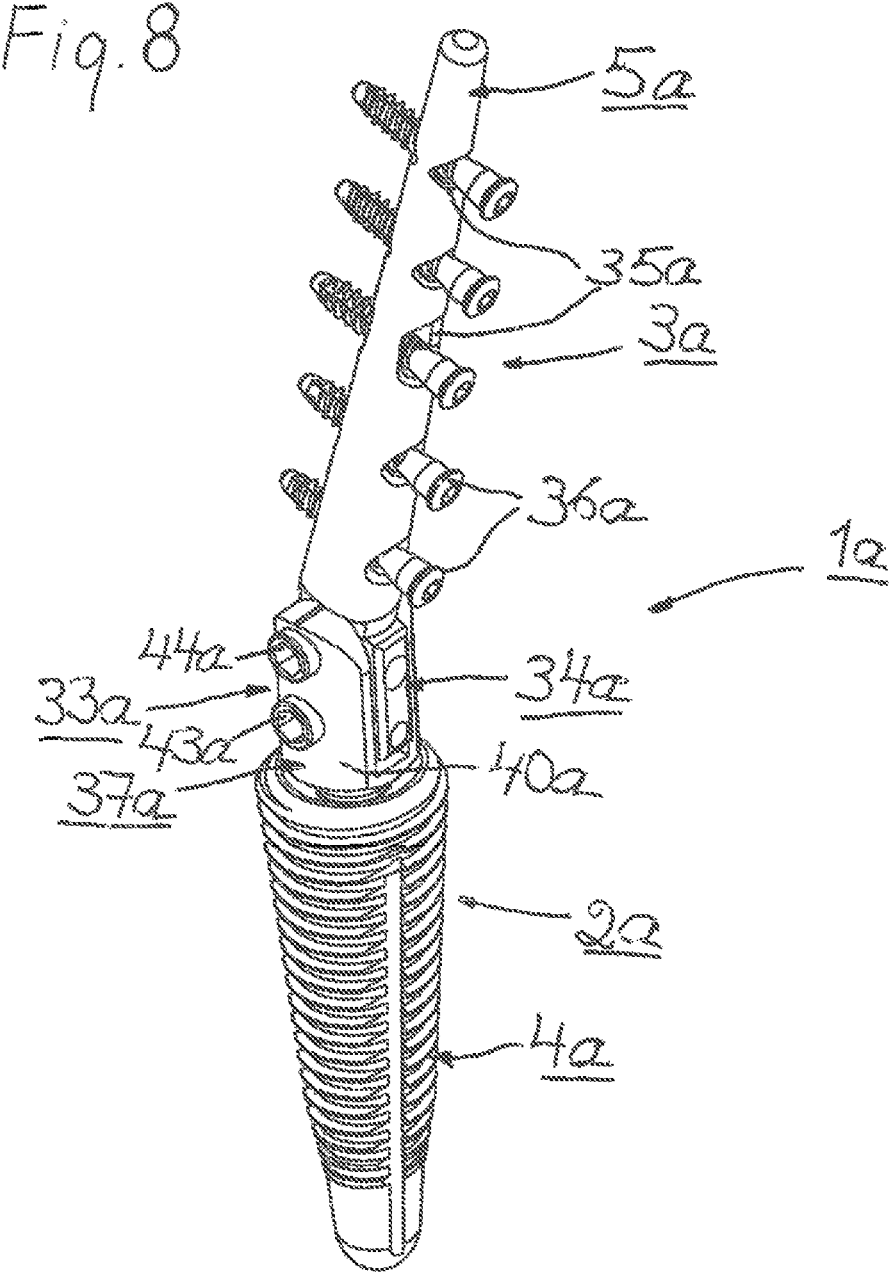

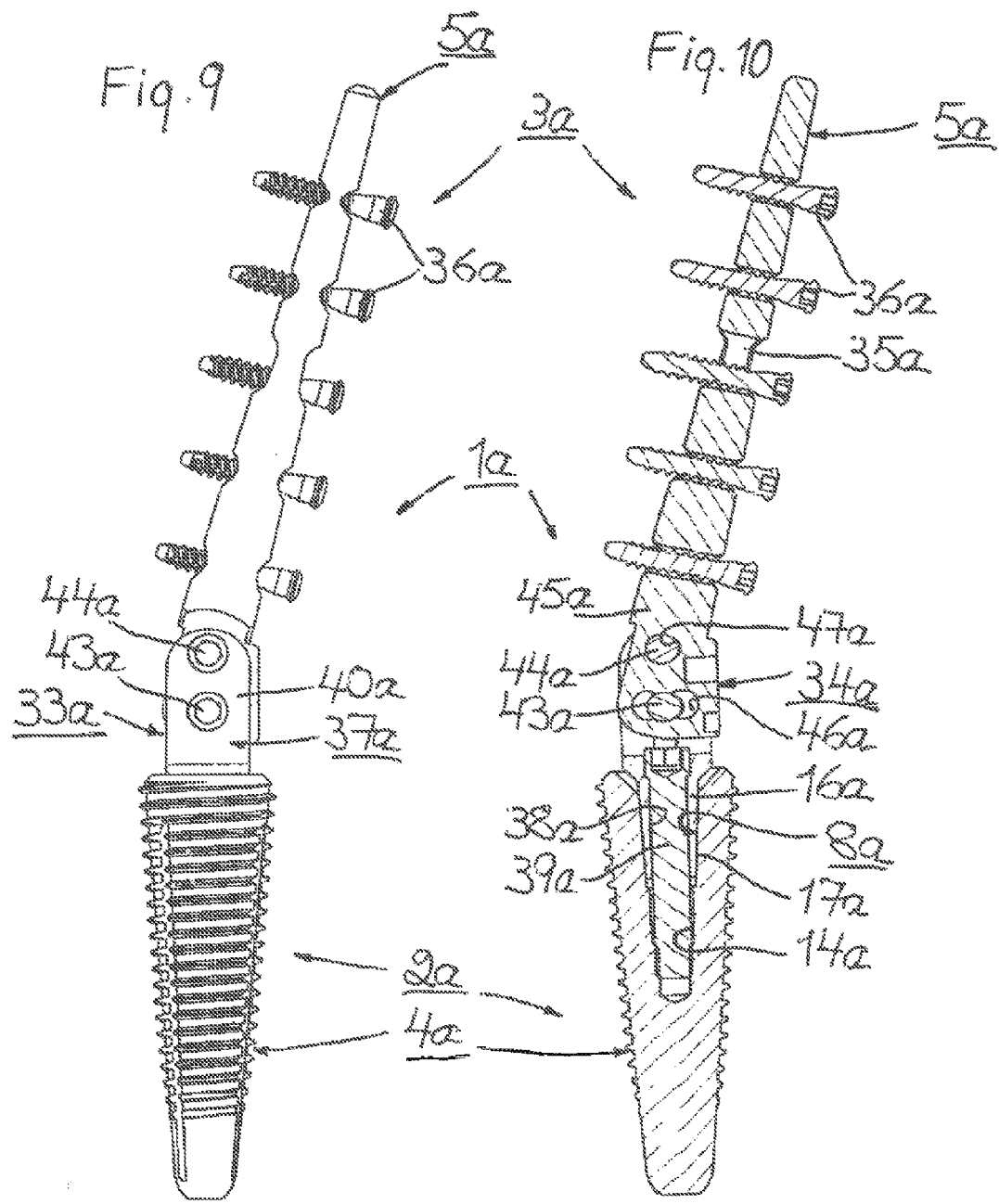

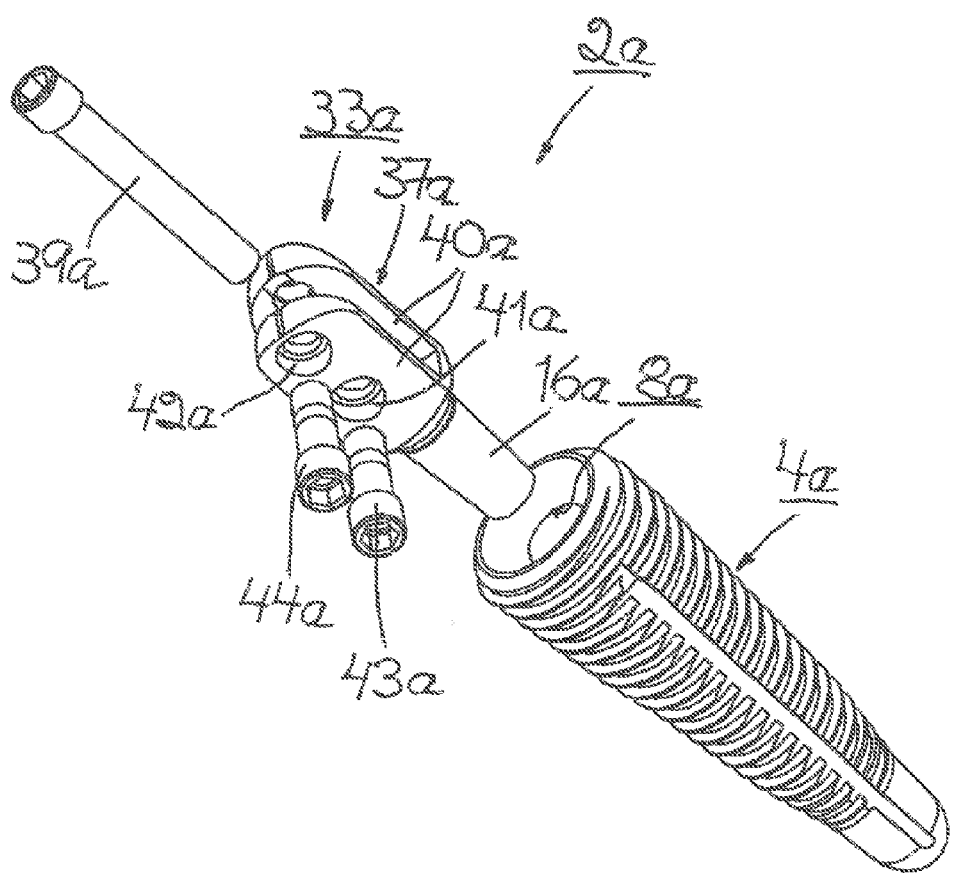

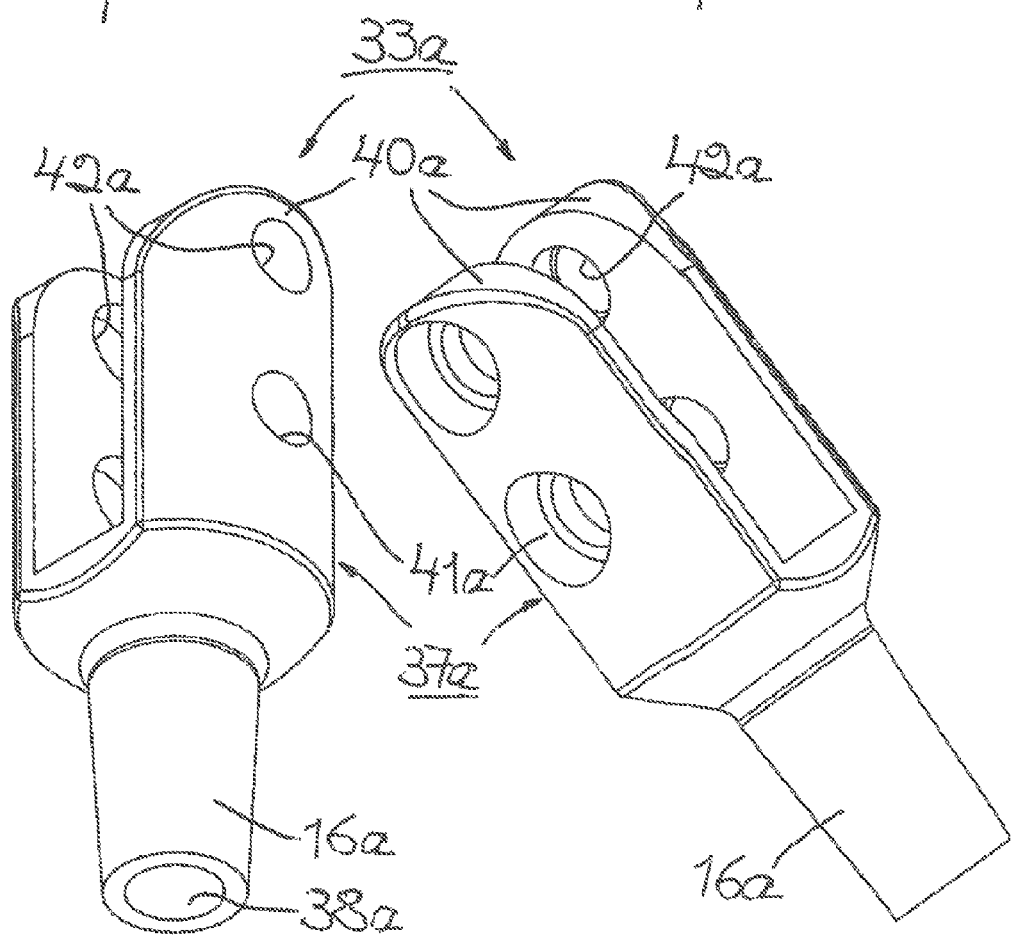

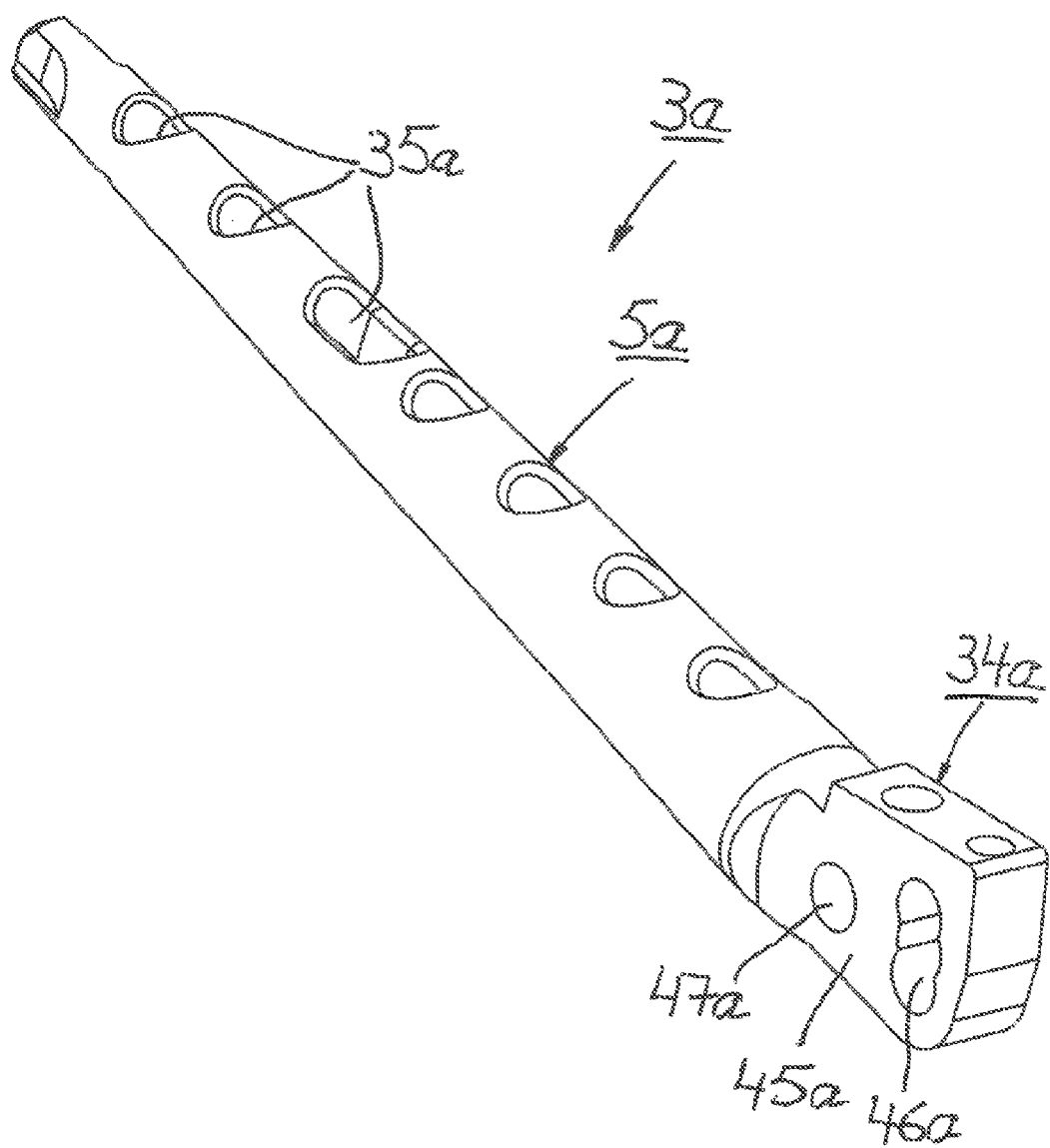

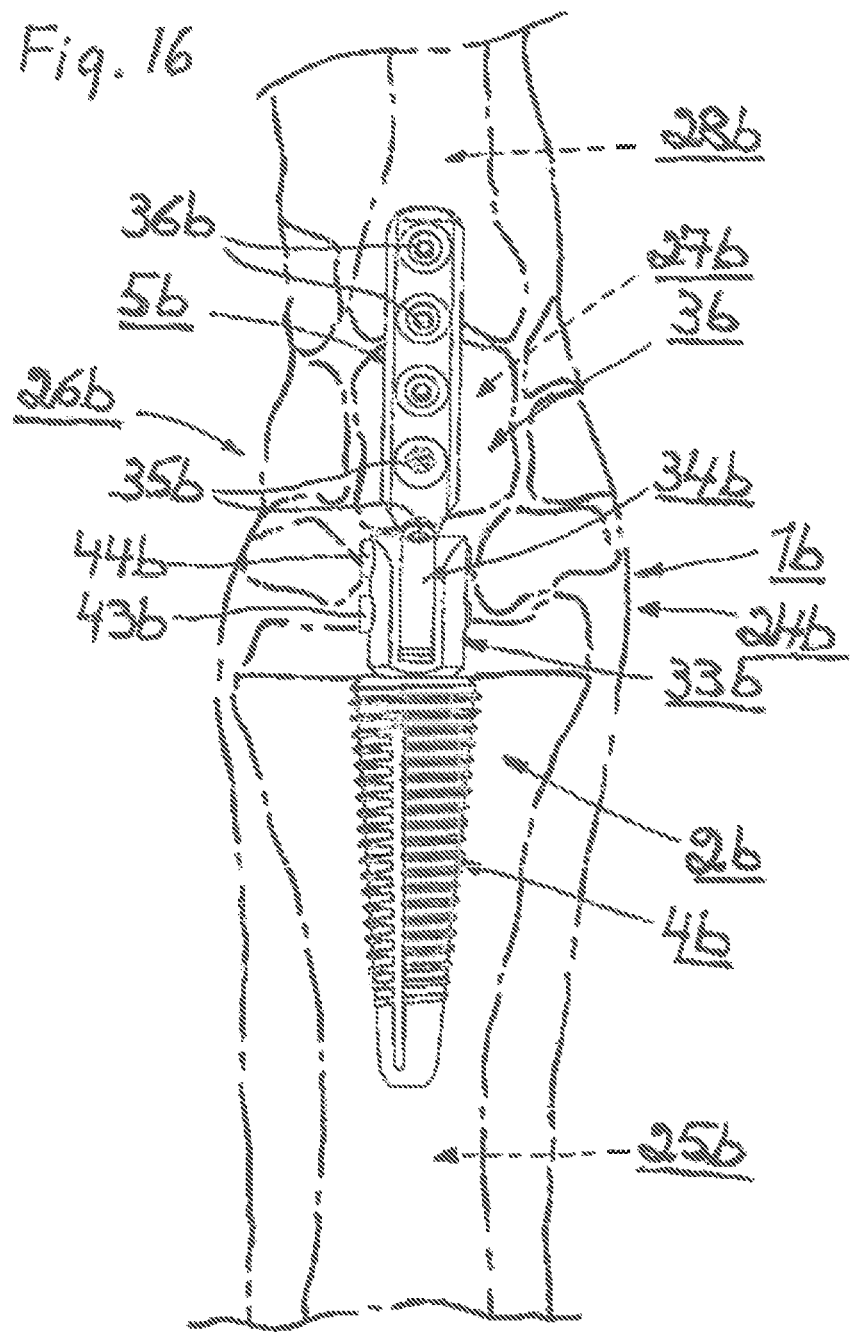

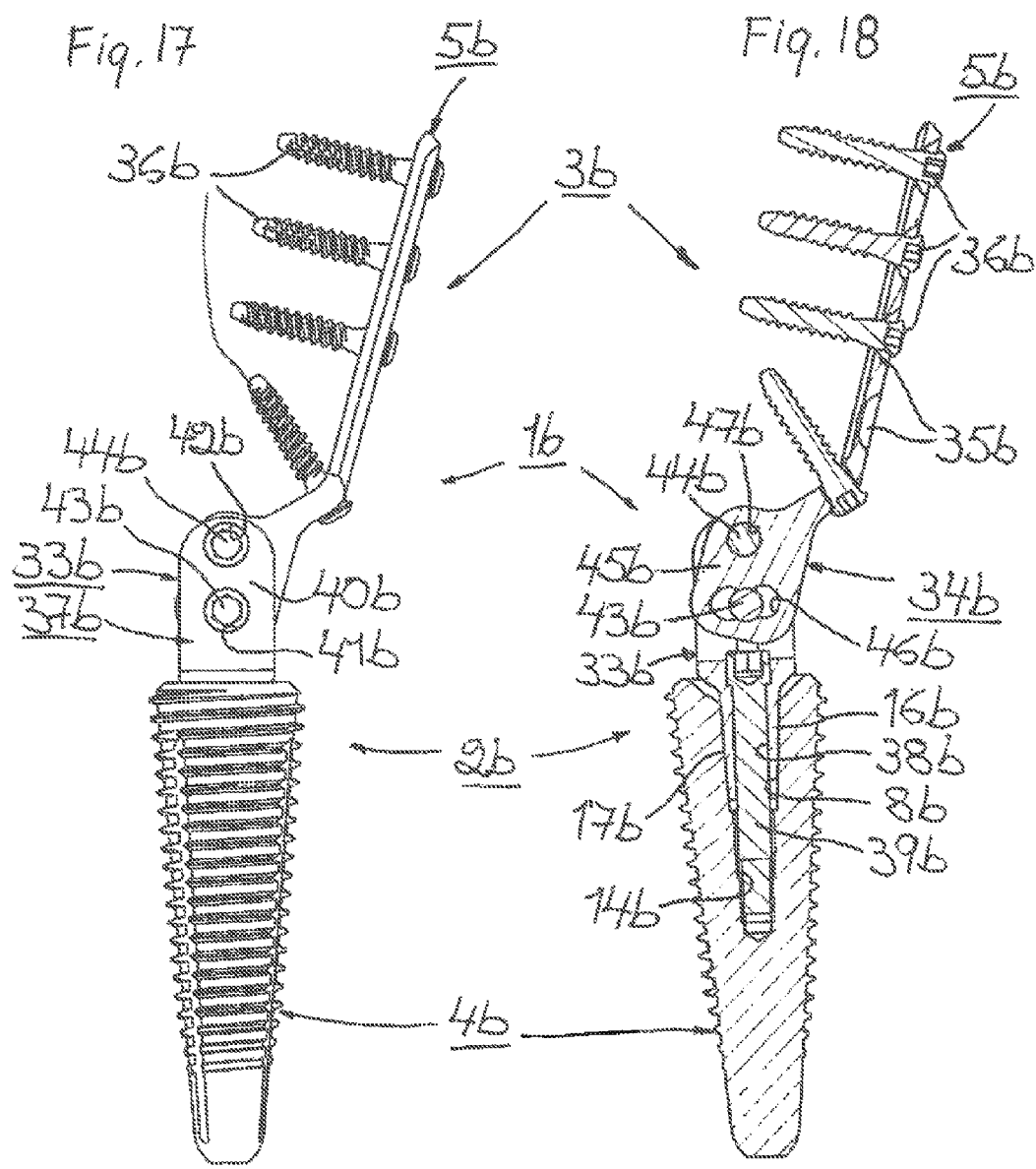

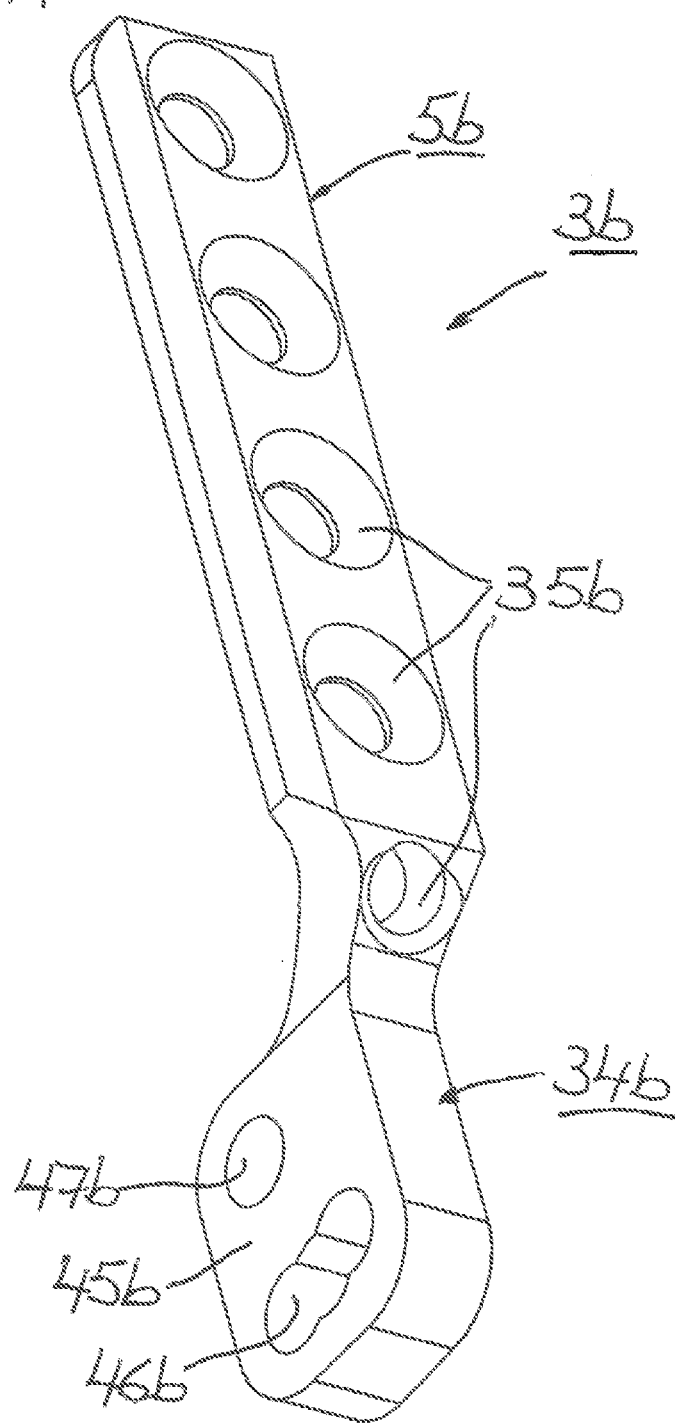

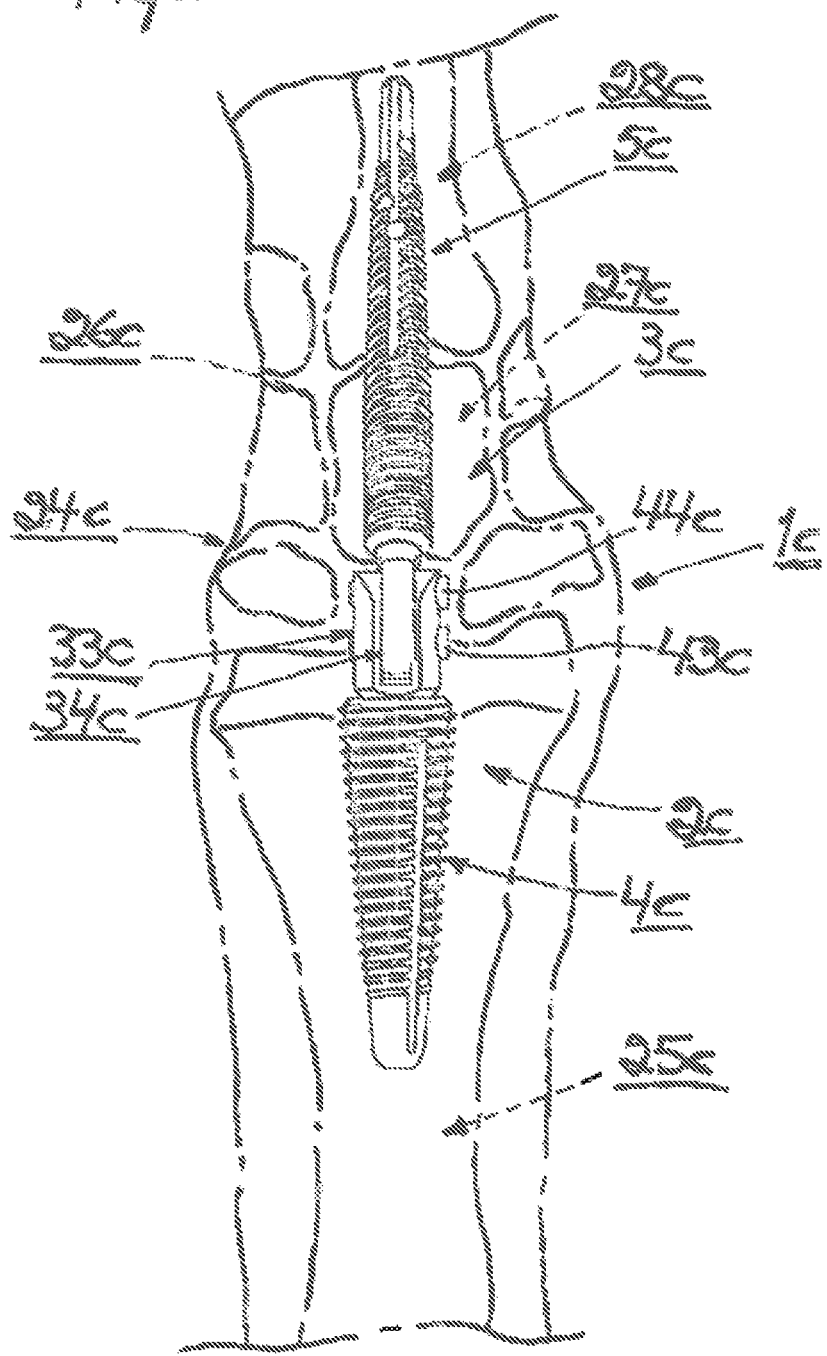

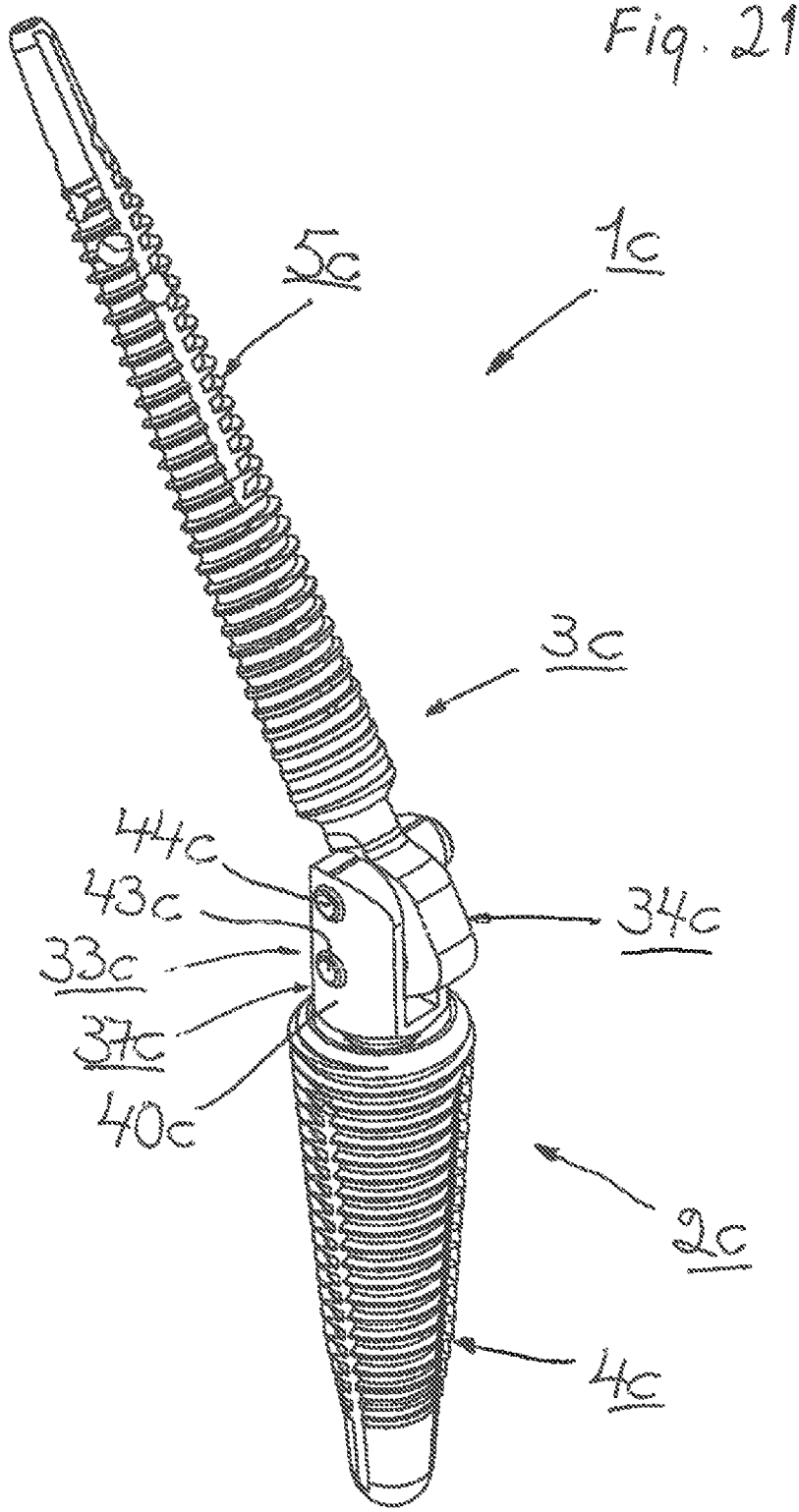

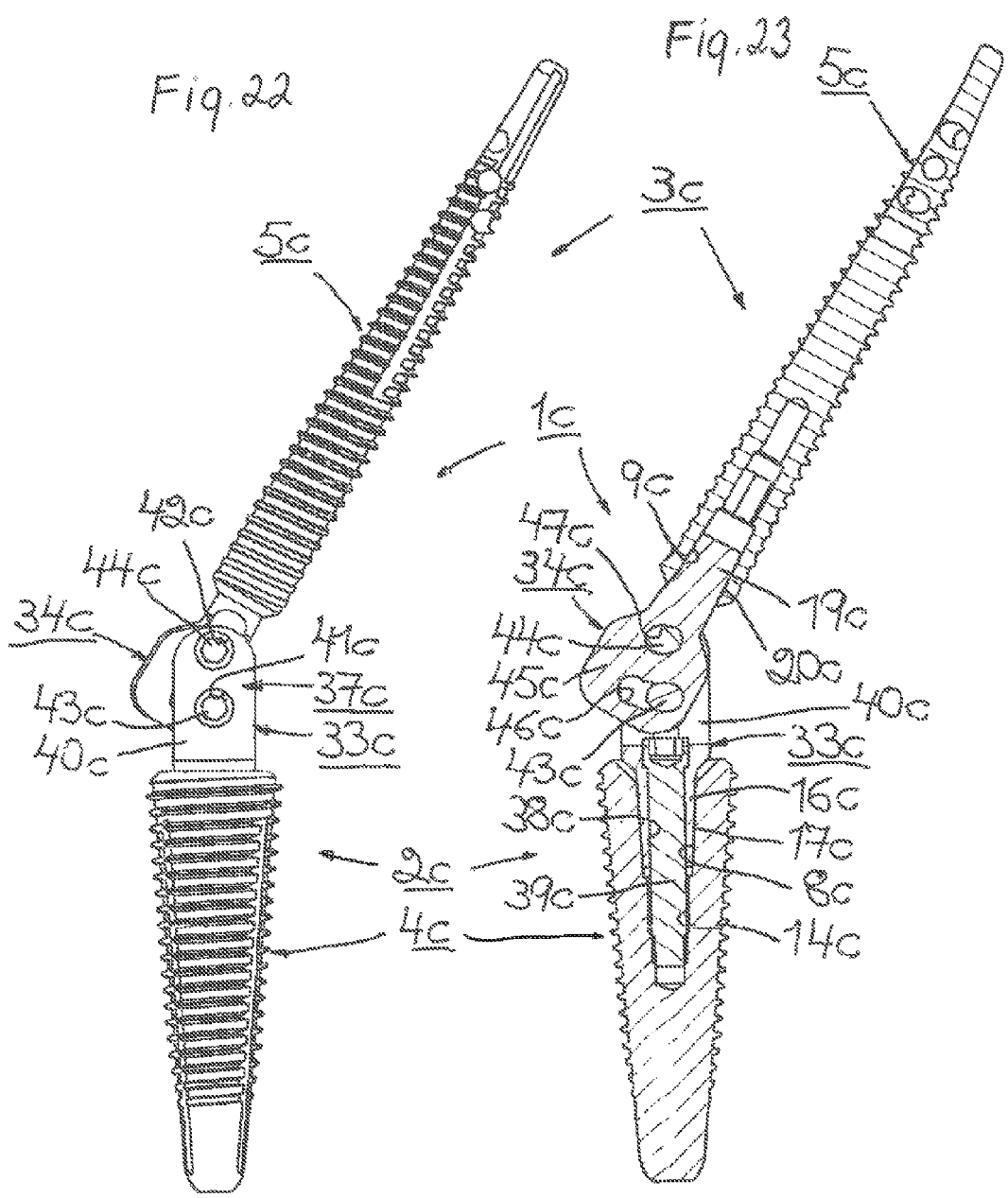

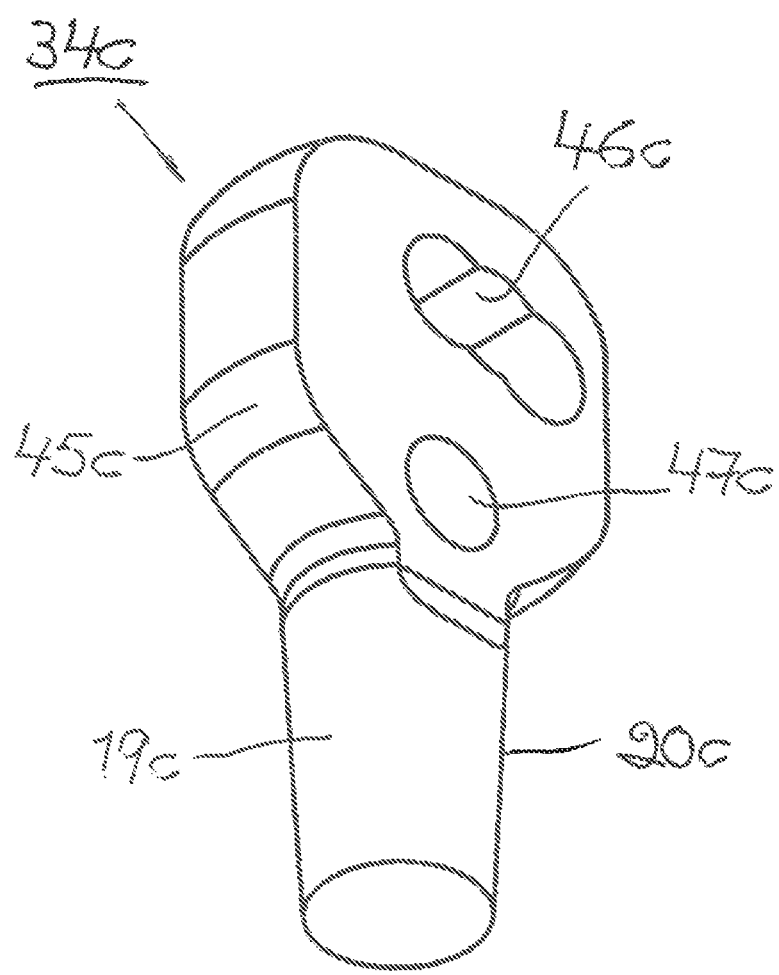

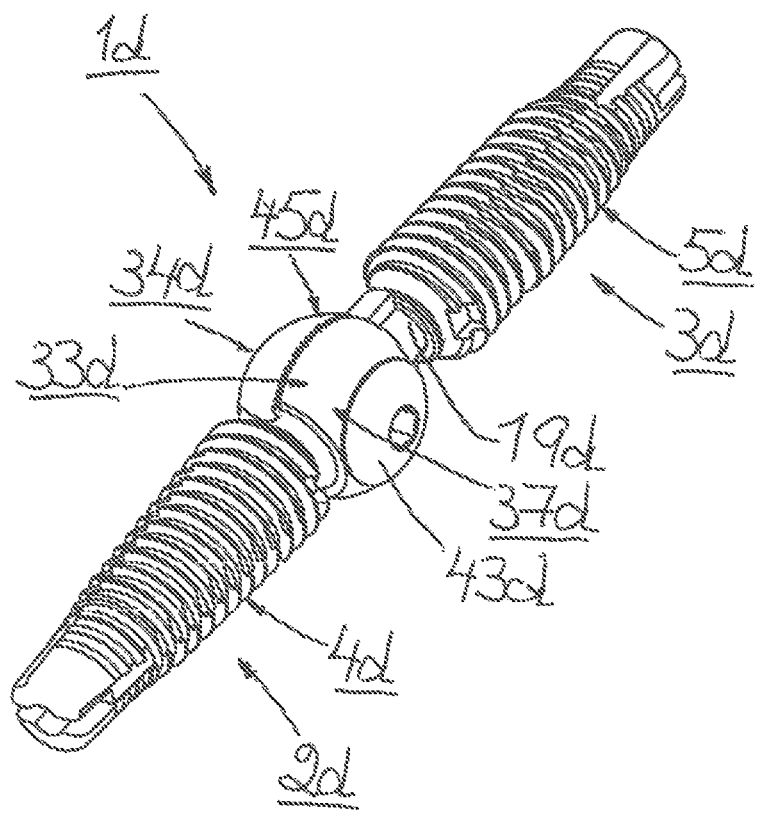

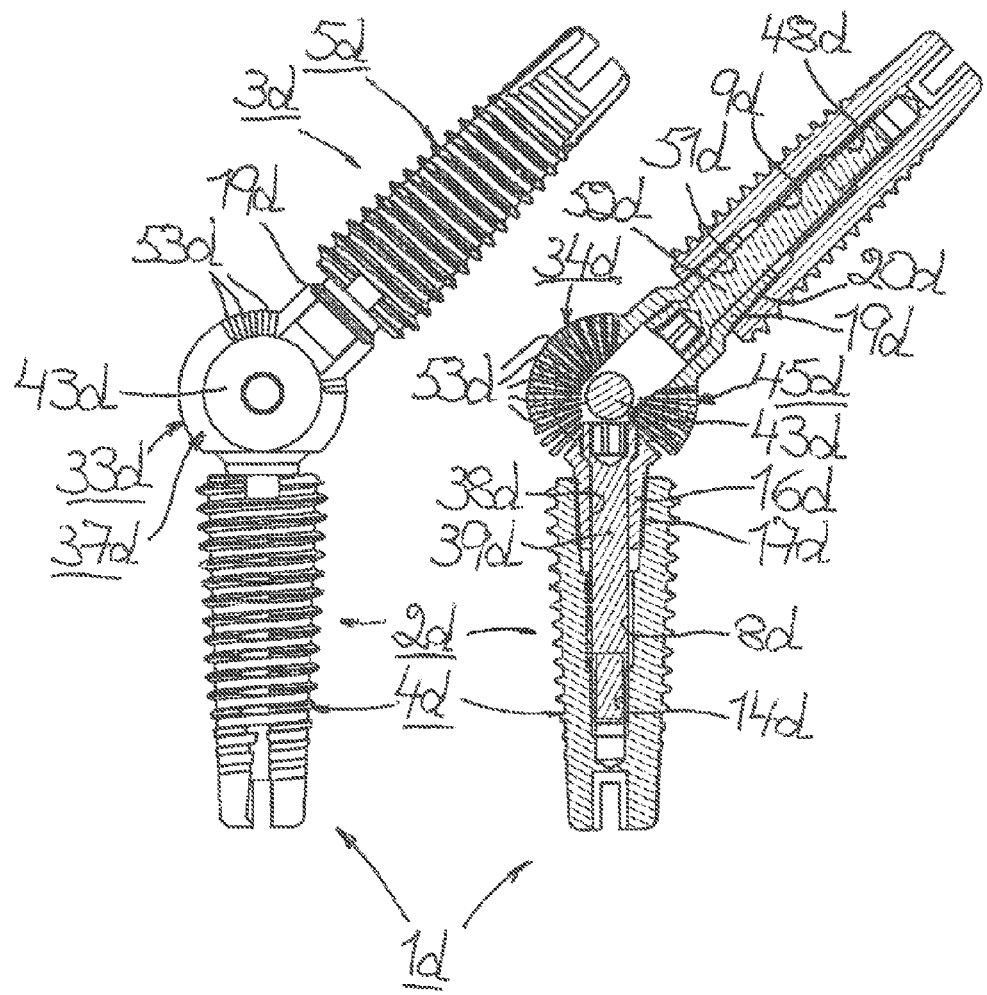

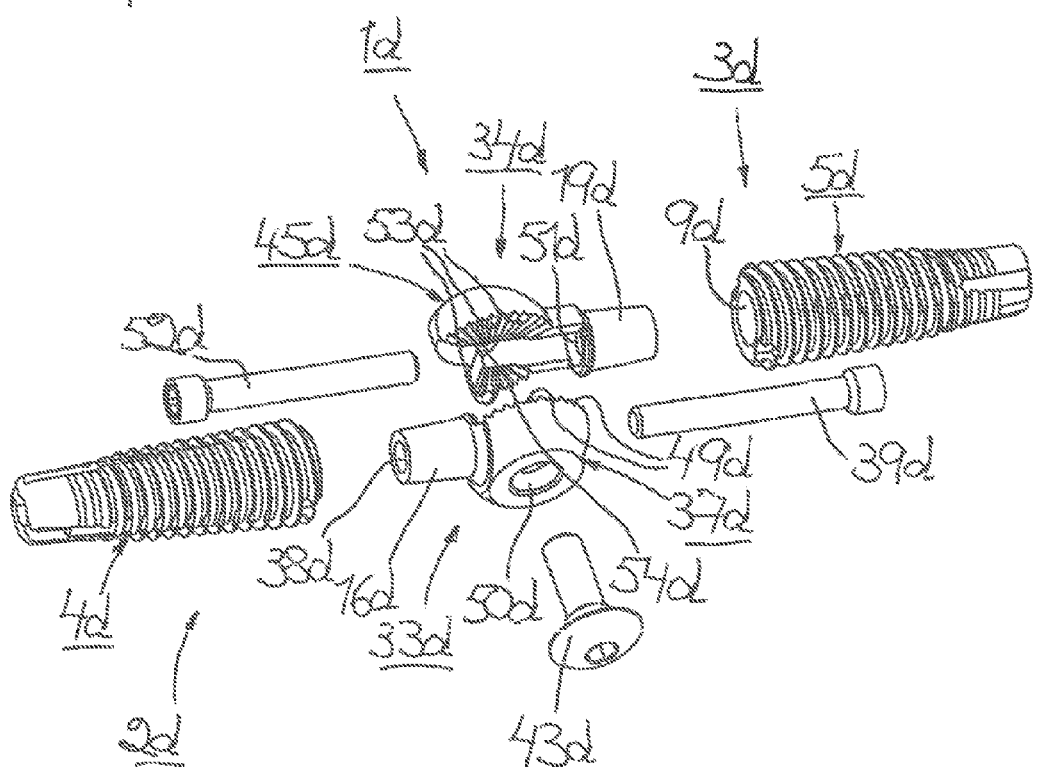

PROSTHESIS

RELATED APPLICATIONS

This application is a divisional of U.S. patent application Ser. No. 13/984,111 filed Sep. 23, 2013, now U.S. Pat. No. 9,445,912, which corresponds to PCT/SE2011/051594, filed Dec. 27, 2011, which claims the benefit of Swedish Application No. 1150197-0, filed Mar. 4, 2011, the subject matter, of which are incorporated herein by reference in their entirety.

TECHNICAL FIELD

The present invention relates to a prosthesis for artrodhesis, wherein the prosthesis comprises two prosthesis members which each is configured for attachment thereof to at least one of the bones at the joint, wherein one of the prosthesis members comprises a first attachment member which is configured for location in at least one of the bones at the joint and the other prosthesis member a second attachment member which is configured for location in at least one other bone at the joint, and wherein said one prosthesis member comprises a locking member and said other prosthesis member a lockable member.

The present invention also relates to a prosthesis for replacement of a joint, wherein the prosthesis comprises two prosthesis members which each is configured for attachment thereof to at least one of the bones at the joint, wherein one of the prosthesis members comprises a first screw-like attachment member which is configured for location in at least one of the bones at the joint and the other prosthesis member a second screw-like attachment member which is configured for location in at least one other bone at the joint, wherein said one prosthesis member comprises a socket member and said other prosthesis member a head member, wherein the socket member is configured with an attachment pin which is insertable into a hole in the first screw-like attachment member for location of the socket member therein, and wherein the head member is configured with an attachment pin which is insertable into a hole in the second screw-like attachment member for location of the head member therein.

BACKGROUND OF THE INVENTION

Prostheses of substantially the above-mentioned construction for artrodhesis already exist in many embodiments.

Examples of such embodiments are found in e.g. US 2010/0130978 A1. One of the draw-backs of this prior art construction is that it is adapted solely for artrodhesis (primary artrodhesis). Should there be a reason for replacing the prosthesis in order to again make the joint flexible, the entire prosthesis must be replaced. Furthermore, the prior art prosthesis does not include any member of the previously used prosthesis for making the joint flexible (artroplasty). Another drawback is the limited possibility to adjust the setting of the pros-thesis members relative to each other and that adjustment must be performed by means of special tools.

Other similar constructions for artrodhesis of e.g. knee joints are found in DE 3347055 A1 and US 2009/0171463 A1.

In SE 528545 C2, a prosthesis for replacement of a joint (artroplasty) is described. This prior art prosthesis is configured substantially as defined above. This prior art construction however, is not adapted for artrodhesis and members thereof can not be used therefor.

SUMMARY OF THE INVENTION

Therefore, the object of the present invention is to provide a simple and yet extensively adjustable prosthesis for use at artrodhesis.

This object is arrived at, at the prosthesis for artrodhesis, by configuring the locking member with an attachment portion which is insertable into a hole in the first attachment member for location of the locking member therein, configuring the lockable member in one piece with the second attachment member and configuring the lockable member for adjustable setting thereof relative to the locking member and for fixation thereof, in set position, to the locking member.

This object is arrived at also by means of a prosthesis with, inter alia, a lockable member which alternatively is configured with an attachment portion which is insertable into a hole in the second attachment member for locating the lockable member therein.

Secondly, it is an advantage, should there be a need, that members of the prosthesis can be used to once again make the joint flexible (artroplasty).

The object of the present invention is also to configure members of a prosthesis for replacing a joint (artroplasty) such that these members can be used for making the joint rigid (artrodhesis).

This object is arrived at, at the prosthesis for artroplasty, by configuring the hole in the first screw-like attachment member at least partly to define a press fit with the attachment pin for the socket member and at least partly with a thread to permit, after removal of the socket member, during artrodhesis, tightening in the hole of a locking member which is configured to cooperate with a lockable member, which can be adjustably set relative to the locking member and fixed thereto in set position, of a second attachment member which replaces the second screw-like attachment member with the head member.

The above object is arrived at also by configuring the locking member to cooperate with a lockable member, which can be adjustably set relative to the locking member and fixed thereto in set position and which replaces the head member in the second screw-like attachment member.

BRIEF DESCRIPTION OF THE DRAWINGS

The invention will be further described in the following with reference to the accompanying drawings, in which

FIG. 7 is a schematic side view of a first embodiment of a prosthesis according to the invention for artrodhesis of a wrist;

FIG. 8 is a schematic perspective view of the prosthesis of FIG. 7;

FIG. 9 is an additional schematic side view of the prosthesis according to FIGS. 7 and 8;

FIG. 10 is schematic sectional view of the prosthesis according to FIG. 9;

FIG. 11 is a schematic perspective view of an attachment member forming part of the prosthesis and with a locking member positionable therein;

FIGS. 12 and 13 are enlarged schematic perspective views of the locking member of FIG. 11;

FIG. 14 is an enlarged schematic perspective view of a somewhat modified attachment member forming part of the prosthesis according to FIGS. 7-10 and with an Integrated lockable member;

FIG. 16 is a schematic side view of a second embodiment of a prosthesis according to the invention for artrodhesis of a wrist;

FIG. 17 is an additional schematic side view of the prosthesis according to FIG. 16;

FIG. 18 is schematic sectional view of the prosthesis according to FIG. 17;

FIG. 19 is an enlarged schematic perspective view of an attachment member forming part of the prosthesis according to FIGS. 16-18 and with an integrated lockable member;

FIG. 20 is a schematic side view of a third embodiment of a prosthesis according to the invention for artrodhesis of a wrist;

FIG. 21 is a schematic perspective view of the prosthesis of FIG. 20;

FIG. 22 is an additional schematic side view of the prosthesis according to FIGS. 20 and 21;

FIG. 23 is schematic sectional view of the prosthesis according to FIG. 22;

FIG. 24 is an enlarged schematic perspective view of the lockable member of the prosthesis of FIGS. 20-23;

FIG. 25 is a schematic perspective view of a fourth embodiment of a prosthesis according to the invention for artrodhesis of a wrist;

FIG. 26 is a schematic side view of the prosthesis according to FIG. 25;

FIG. 27 is schematic sectional view of the prosthesis according to FIG. 26; and

FIG. 28 is an exploded view of the prosthesis according to FIGS. 25-27.

DETAILED DESCRIPTION OF PREFERRED EMBODIMENTS

Figure 1:
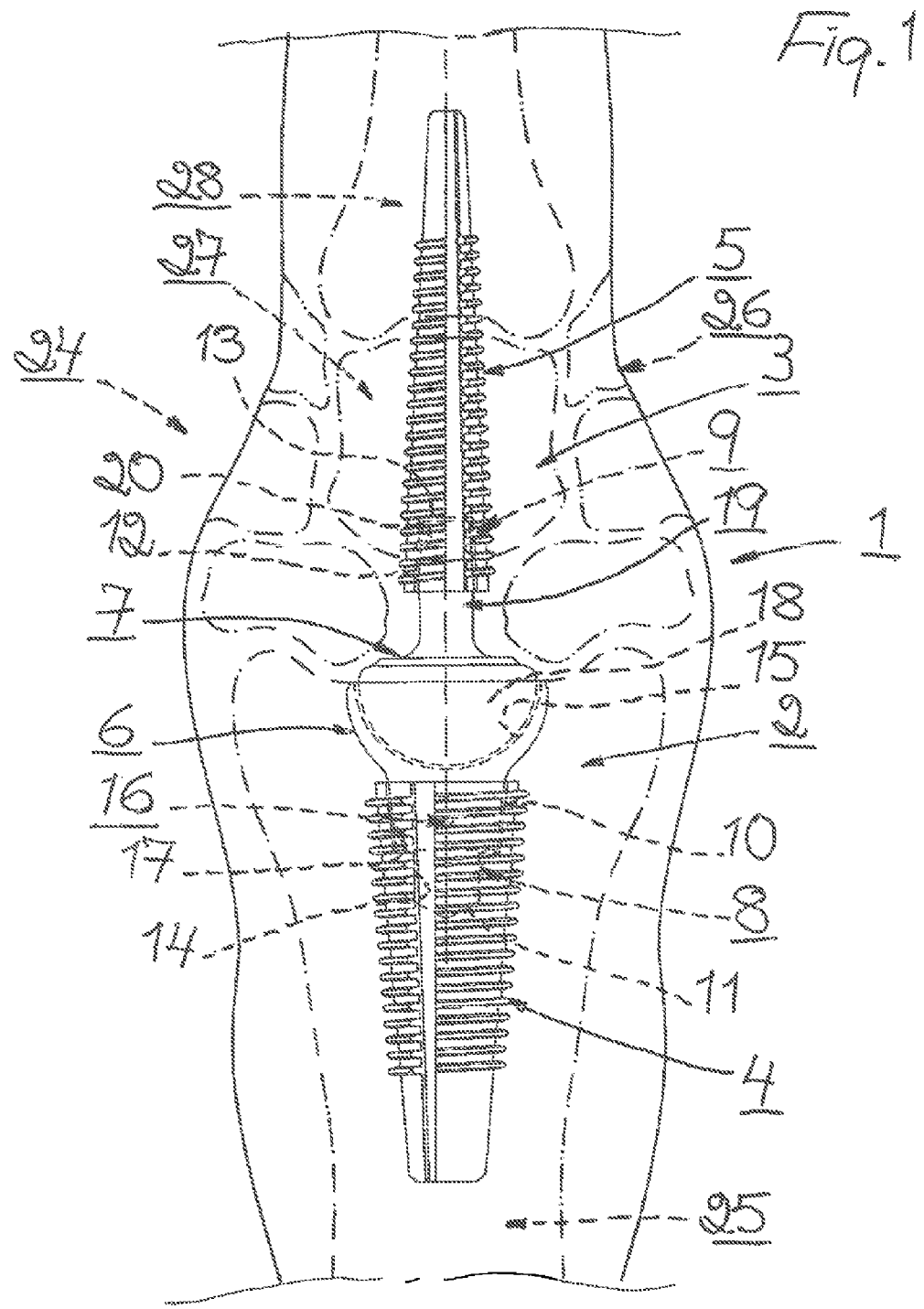
FIG. 1 is schematic side view of a prosthesis according to the invention for replacement of a joint (artroplasty), here a wrist, with screw-like attachment members of the prosthesis configured for artrodhesis of the wrist.

Thus, FIG. 1 illustrates a prosthesis according to the present invention for replacement of a wrist in order to preserve or maintain the flexibility of the wrist. This prosthesis is already described in SE 528545 C2, to which reference is made for further details. Therefore, the prosthesis will here be described in general terms only. The wrist prosthesis 1 comprises a first prosthesis member 2 and a second prosthesis member 3. The first prosthesis member 2 comprises a first screw-like attachment member 4 and the second prosthesis member 3 a second screw-like attachment member 5. The first prosthesis member 2 also comprises a socket member 6 and the second prosthesis member 3 a head member 7.

Each first and second screw-like attachment member 4, 5 is configured with a hole 8 and 9 respectively. The hole 8 in the first screw-like attachment member 4 extends in the form of a depression at a first end edge at which said attachment member has its largest diameter in an axial direction towards a second end edge of said attachment member at which the attachment member has its smallest diameter. The hole 9 in the second screw-like attachment member 5 extends as a depression at a first end edge at which said attachment member has its largest diameter in an axial direction towards a second end edge of said attachment member at which the attachment member has its smallest diameter.

The hole 8 in the first screw-like member 4 has its largest diameter at the first end edge and its side walls 10 have at least partly a conical shape, such that the hole tapers conically towards the bottom 11 of the hole. The hole 9 in the second screw-like member 5 has its largest diameter at the first end edge and its side walls 12 have at least partly a conical shape, such that the hole tapers conically towards the bottom 13 of the hole.

The hole 8 in the first screw-like member 4 is also at least in part provided with a thread 14.

The socket member 6 has a socket 15 defining a concave joint surface. An attachment pin 16 extends axially from the outer side of the socket 15. The attachment pin 16 has an axial outer side 17 which tapers conically towards its end edge. The shape and size of the attachment pin 16 and the shape and size of the hole 8 in the first screw-like attachment member 4 are chosen such that they, when pressed together in an axial direction, form a press fit, i.e. a connection which permits the socket member 6 and the first screw-like attachment member 4 to be brought to attach to each other when pressed together.

The head member 7 has a substantially spherical head 18 defining a convex joint surface of such shape that it fits into the joint surface of the socket 15 such that said joint surfaces can slide against each other and enable the flexibility of the joint. An attachment pin 19 extends axially from the outer side of the head 18. The attachment pin 19 has an axial outer side 20 which tapers conically towards its end edge. The shape and size of the attachment pin 19 and the shape and size of the hole 9 in the second screw-like attachment member 5 are chosen such that they, when pressed together in an axial direction, form a press fit, i.e. a connection which permits the head member 7 and the second screw-like attachment member 5 to be brought to attach to each other when pressed together.

The first and second screw-like attachment members 4, 5 are within the holes 8, 9 con-figured with additional holes (not shown) to permit a screw pin 21 of a screw tool 22, e.g. a screw driver, to be inserted into the holes for tightening or securing by screwing the screw-like attachment members in the respective bone. The holes for the screw tool 22 are not round, e.g. multi-edge holes such as hexagonal holes or similar.

Each first and second screw-like attachment member 4, 5 is at the illustrated embodiment tapering conically from the first end edge in a direction towards the second end edge. The conical shape can extend the entire distance between said end edges, but this is not a requirement. Each first and second screw-like attachment member 4, 5 is also configured with external threads for tightening of the attachment members in the respective bone. The external threads may have self-tapping properties and extend in different degrees along the screw-like attachment members 4, 5.

Each first and second screw-like attachment member 4, 5 may be configured with an axial through-hole (not shown) such that the attachment member can be threaded onto a guide wire 23 which is adapted for arrangement at the respective bone and which is adapted to guide the attachment members when these members are screwed into the respective bone.

The illustrated prosthesis may, as stated above, be provided at a wrist 24 for replacement thereof and at the same time maintain most of the flexibility in said wrist (artroplasty). The bones in such a wrist and bones in the hand and arm are shown schematically in FIG. 1 with broken lines and these bones may be the radius 25, one or more bones in carpus 26, e.g. the capitate 27, and a metacarpal bone 28, e.g. the third metacarpal bone. As is apparent in FIG. 1, the first screw-like attachment member 4 is screwed into the radius 25 and is therefore configured thicker and shorter than the second screw-like attachment member and it has a larger hole 8 than the hole 9 in the second attachment member. The second screw-like attachment member 5 is at the Illustrated wrist 24 screwed into the capitate 27 and the metacarpal bone 28.

FIGS. 2-6 illustrate how the first and second screw-like attachment members 4, 5 can be provided in the respective bone 25, 27 and 28.

Figure 2:
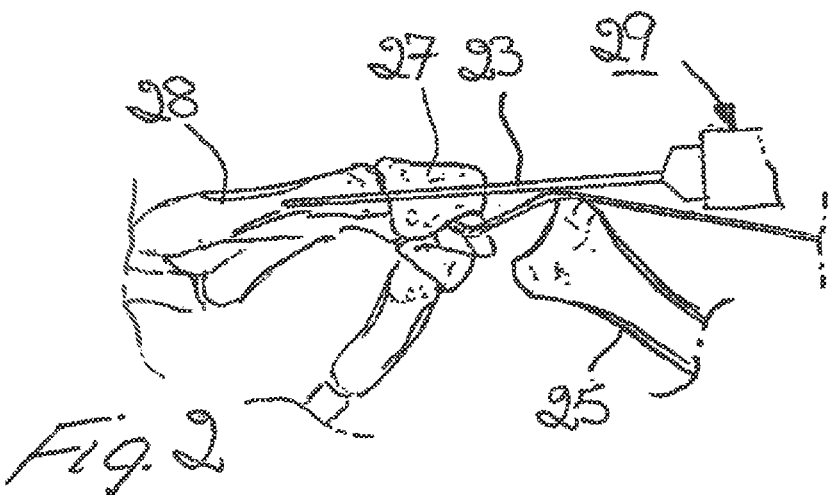
FIGS. 2-6 are schematic side views of different moments during location of the screw-like attachment members forming parts of the prosthesis according to FIG. 1.

As shown in FIG. 2, a guide wire 23 which is attached to a drilling machine 29, is drilled through the capitate 27 and into the metacarpal bone 28. Then, the drilling machine 29 is removed, while the guide wire 23 is left in position.

Figure 3:
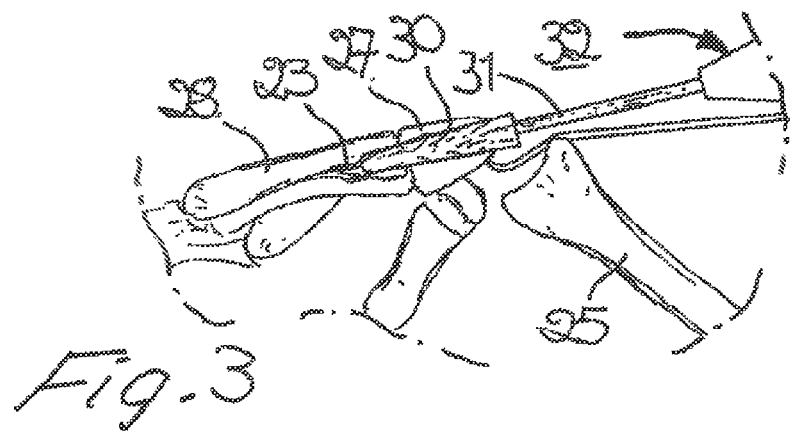

As illustrated in FIG. 3, a conical drill 30 and a tubular bracket 31 by means of which the drill 30 is mounted on a drilling machine 32, are then threaded onto the guide wire 23 and conical holes are drilled in the capitate 27 and the metacarpal bone 28.

Figure 4:
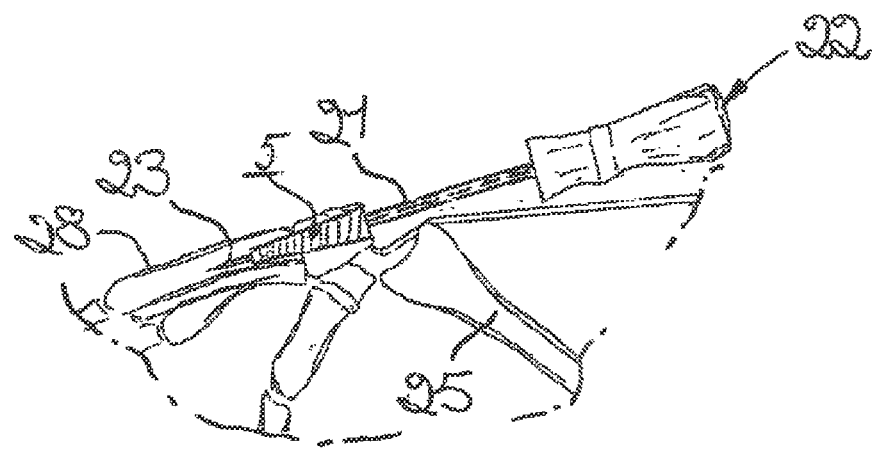

As illustrated in FIG. 4, the second screw-like attachment member 5 is then threaded onto the guide wire 23. Thereafter, the cannulated screw pin 21 of the screw driver 22 is threaded onto the guide wire 23 and into the hole for the screw driver in the second screw-like attachment member 5, the screw driver is rotated for tightening or securing by screwing said attachment member in the holes in the capitate 27 and the metacarpal bone 28. Finally, the screw driver 22 and the guide wire 23 are removed.

Figure 5:
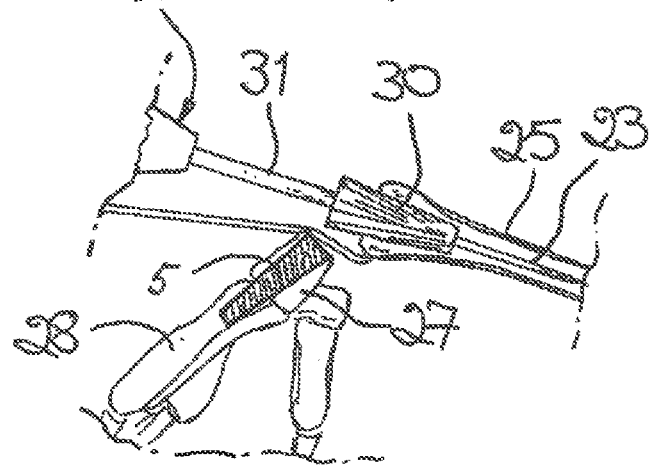
Figure 6:
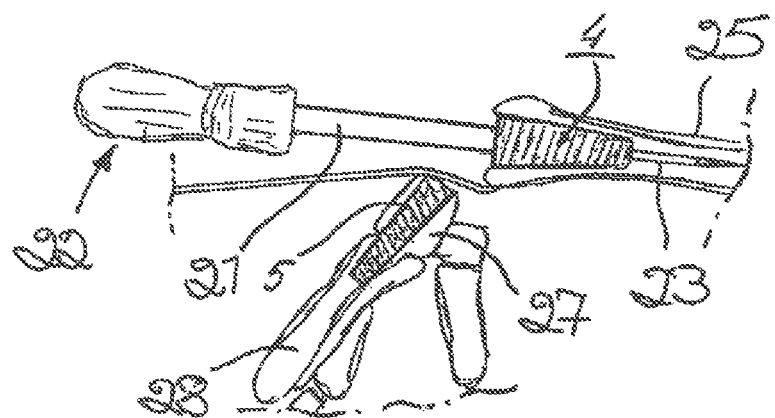

As is apparent from FIGS. 5 and 6, the same procedure is used for providing the first screw-like attachment member 4 in the radius 25. Thus, it is apparent from FIG. 5 that a guide wire 23 is fixedly attached to the radius 25, that a conical drill 30 (which is larger than the drill 30 in FIG. 3) is threaded onto the guide wire and that one has drilled a conical hole in the radius by means of said drill. In FIG. 6, it is shown that one has tightened or secured by screwing the first screw-like attachment member 4 in the radius 25 by means of the screw driver 22 and has then removed the guide wire 23 from the radius.

The first and second screw-like attachment members 4, 5 may consist of at least one material, while the socket and head members 6, 7 may consist of at least one other material. Thus, each first and second screw-like attachment member 4, 5 may comprise a core of a metal and an outer layer of a material which can be dissolved when said attachment members are implanted.

Said core may consist of a titanium alloy and the dissolvable material may consist of or include calcium phosphate.

The socket and head members 6, 7 may consist of a chromium-cobalt-alloy.

The prosthesis 1 described above is, as mentioned, adapted for replacing a wrist for maintaining its flexibility. However, the first screw-like attachment member 4 of the prosthesis 1 may when required be used also for artrodhesis. To this end, the hole 8 in the first screw-like attachment member 4 is at least in part configured to define a press fit with the attachment pin 16 for the socket member 6 and is at least partly threaded (thread 14) to permit tightening in the hole of a locking member (33a; 33b, see preferably FIGS. 12 and 13 showing the locking member 33a) after removal of said socket member, said locking member being configured to cooperate with a lockable member (34a; 34b, see FIG. 13 and, alternatively, FIG. 17) of a second attachment member (5a; 5b, see FIG. 14; 19) replacing the second screw-like attachment member 5 with the head member 7, said lockable member being configured to be adjustably set relative to the locking member and fixed thereto in set position. The prosthesis 1 will hereby be configured substantially as the prosthesis 1a according to FIGS. 7-10 or as the prosthesis 1b according to FIGS. 16-18.

Alternatively, if the second screw-like attachment member 5 is undamaged and has not loosened from the surrounding bone tissue, the locking member (33c, with the same con-figuration as the locking member 33a according to FIGS. 12 and 13; 33d) is configured to cooperate with a lockable member (34c, see FIG. 24; 34d, see FIG. 28) which replaces the head member 7 in the second screw-like attachment member 5, and which is configured to be adjustably set relative to the locking member and fixed thereto in set position. The prosthesis 1 will hereby be configured substantially as the prosthesis 1c according to FIGS. 20-23 or as the prosthesis 1d according to FIGS. 25-28.

The hole 9 in the second screw-like attachment member will then be configured to define a press fit also with the lockable member (34c, see FIG. 24), alternatively also configured with a thread for tightening or securing by screwing in the lockable member (34d, see FIG. 27).

At a primary artrodhesis, i.e. when a decision has been taken that an artrodhesis of in this case a wrist must be performed immediately, the prosthesis is of course in principal constructed in a corresponding way as the prosthesis 1 described above.

Thus, the prosthesis 1a of FIGS. 7-15 for a wrist 24a comprises, as previously, a first pros-thesis member 2a and a second prosthesis member 3a. The first prosthesis member 2a comprises a first attachment member 4a and the second prosthesis member 3 a second attachment member 5a. The first prosthesis member 2a also comprises a locking member 33a instead of a socket member 6 and the second prosthesis member 3 a lockable member 34a instead of a head member 7.

The first attachment member 4a is in the illustrated embodiment configured as a screw, but can also have another shape.

The second attachment member 5a is in the embodiment of FIGS. 7-15 made in one piece, i.e. integral with the lockable member 34a. The second attachment member 5a comprises thereby an elongated, from the lockable member 34a substantially conically tapering member with transversely through said member and substantially in line in the longitudinal direction thereof configured holes 35a for means 36a for fixation or attachment of said second attachment member in the capitate 27a and the metacarpal bone 28a. In the illustrated embodiment, the second attachment member 5a has five (or seven, FIG. 14) holes 35a for attachment means 36a. At least one of the holes 35a is a long-hole for reasons described below and said attachment means 36a consist of so called cortical screws.

The first attachment member 4a is configured with a hole 8a. This hole 8a has in turn at least partly a conical shape and is at least partly configured with a thread 14a, as is the hole 8.

The locking member 33a is configured with an attachment portion 16a, e.g. an attachment pin, which is insertable into the hole 8a in said first attachment member 4a for location of the locking member therein. Accordingly, the attachment portion 16a has a conically tape-ring outer side 17a. The shape and size of the attachment portion 16a and the shape and size of the hole 8a in the first attachment member 4a are chosen such that they, when pressed together in an axial direction, form a press fit, such that the locking member 33a and the first attachment member 4a can be brought to attach to each other by pressing said members together.

The lockable member 34a is adjustably settable relative to the locking member 33a and in set position fixable to the locking member.

Except for the attachment portion 16a, the locking member 33a is also configured with a locking portion 37a which is connected to the attachment portion. The locking portion 37a is configured for fixation or attachment of the lockable member 34a thereto. The attachment portion 16a is configured with a hole 38a which extends through said attachment portion and in the longitudinal direction thereof for insertion therein of a partly threaded attachment means 39a for tightening or securing by screwing the locking member 33a to the first attachment member 4a by bringing said attachment means to cooperate with the threaded portion 14a of the hole 8a in said first attachment member. The locking portion 37a of the locking member 33a is in the illustrated embodiment substantially U-shaped and comprises two shanks 40a with holes 41a, 42a provided in said shanks opposite each other. Each shank 40a is in the illustrated embodiment configured with two holes 41a, 42a which extend through the shank and substantially in line in the longitudinal direction of the locking portion 37a. One hole 41a is configured for a locking means 43a (inclination screw) for fixation or attachment of the lockable member 34a to the locking member 33a and the other hole 42a is configured for an axis 44a about which the lockable member can pivot for adjustable setting thereof relative to the locking member.

Correspondingly, the lockable member 34a comprises in the illustrated embodiment a substantially flange-like lockable portion 45a for insertion between the shanks 40a of the locking portion 37a of the locking member 33a. The flange-like lockable portion 45a is configured with a curved long-hole 46a, which extends transversely therethrough, for said locking means 43a and with a hole 47a, also extending transversely through said lockable portion, for the axis 44a about which the lockable member can pivot for adjustable setting thereof relative to the locking member. At insertion of the flange-like lockable portion 45a between the shanks 40a of the locking portion 37a of the locking member 33a, portions of the long-hole 46a are brought in line with the holes 41a for the locking means 43a in said shanks for fixation or attachment of the lockable portion to the locking portion of the locking member and the hole 47a for the pivoting axis 44a is brought in line with the holes 42a for said pivoting axis in said shanks. The lockable portion 45a of the lockable member 34a may have another shape than the flange-like shape as long as it fulfils its function and permits insertion thereof between the shanks 40a of the locking portion 37a of the locking member 33a. The long-hole 46a in the lockable portion 45a of the lockable member 34a is configured with a plurality of, e.g. three fixed positions (see e.g. FIGS. 10 and 14) corresponding with different angular positions of the lockable member relative to the locking member.

Figure 15:
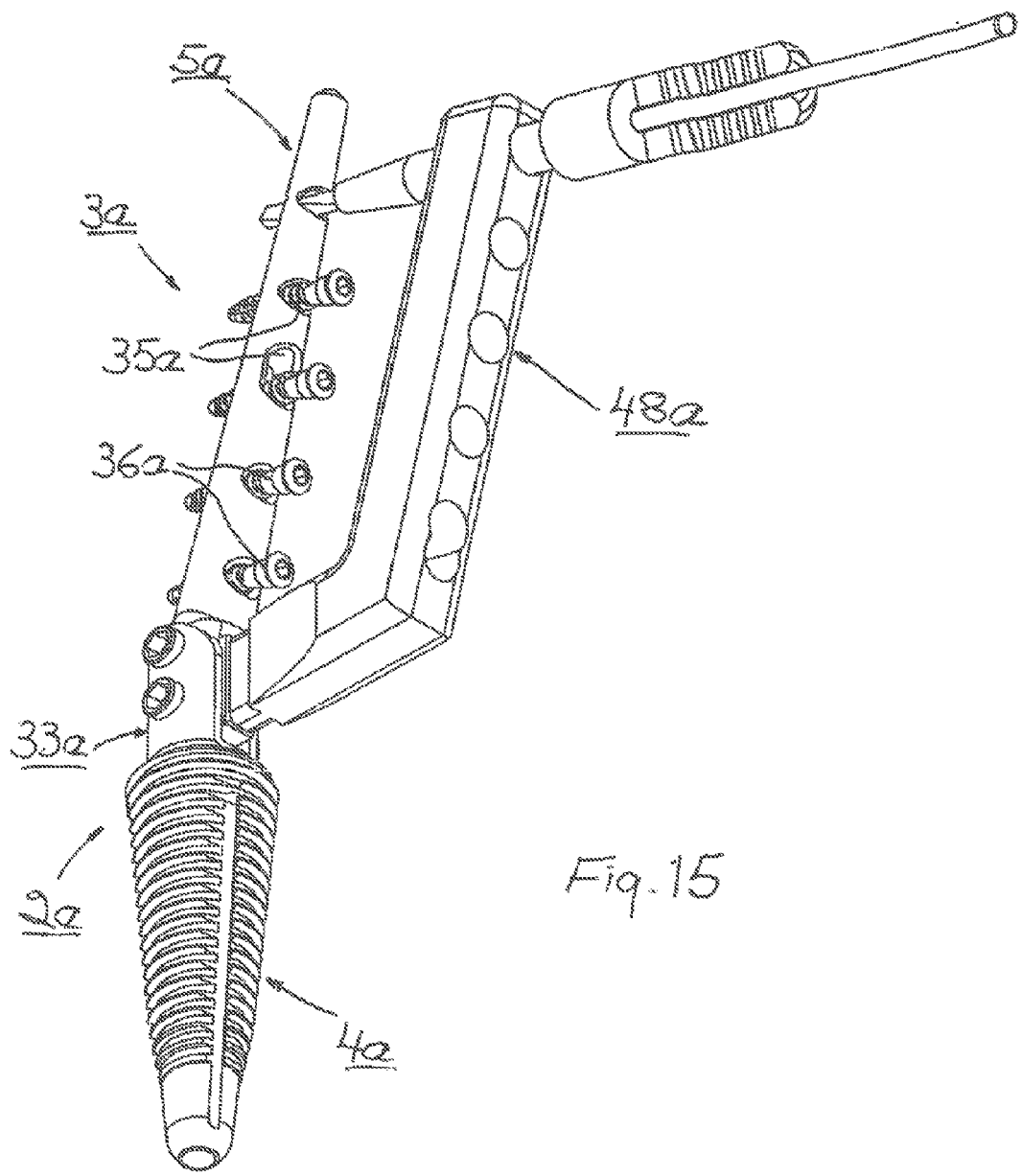
FIG. 15 illustrates schematically, except for the prosthesis, an instrument by means of which the attachment member with integrated lockable member is located in at least one bone.

In FIGS. 11 and 15, it is partly illustrated how the wrist prosthesis 1a is provided after the first attachment member 4a has been screwed into and attached to the radius 25a, alter-natively after all members of an articulated prosthesis 1 according to FIG. 1 but the first attachment member 4 have been removed.

Thus, in FIG. 11 it is shown how the locking member 33a is located in the first attachment member 4a by inserting the attachment portion 16a of said locking member into the hole 8a in said attachment member and the locking member is tightened or secured by screwing in the hole by means of the attachment means 39a which, after it has been moved or screwed through the hole 38a in the attachment portion of the locking member, is brought to cooperate with the thread 14a in the hole 8a in said attachment member. The tightening by screwing of the attachment means 39a as described is performed by means of a screw tool of a suitable type. The locking member 33a is by rotation thereof brought to a suitable position in order to permit a suitable setting of the prosthesis in the medial-lateral plane before the locking member is fixed by tightening of the attachment means 39a. Accordingly, the attachment means 39a has two functions, namely to lock the locking member 33a axially to the first attachment member 4a and to lock the locking member to the first attachment member such that said locking member, after a suitable rotation there-of, no longer can rotate due to the friction caused by the axial pressure between the lock-in member and the attachment member.

After insertion of the second attachment member 5a with lockable member 34a in the drilled passage in the capitate 27a of carpus 26a and in the metacarpal bone 28a, the lockable portion 45a of the lockable member is fit in between the shanks 40a of the locking portion 37a of the locking member 33a and the lockable member is attached to the locking member by means of a screw 44a defining the pivoting axis, said screw being inserted into the holes 42a, 47a in said members. By means of the U-shaped configuration of the locking member 33a and the configuration of the lockable member 34a fitting thereto, these members may be provided or located separately and then assembled or mounted together without maximum stretching of the hand.

In FIG. 15 it is to a certain extent illustrated how the second attachment member 5a is fixed in the capitate and in the metacarpal bone. A first cortical screw 36a is screwed through the hole 35a shaped as a long-hole and locks the second attachment member 5a in the capitate 27a or the metacarpal bone 28a, depending on where the long-hole is situated, for possible necessary compression of the prosthesis 1a. After compression, additional cortical screws 36a are screwed into the remaining holes 35a in the second attachment member 5a and fix thereby said attachment member in the capitate and the metacarpal bone. During tightening of the cortical screws 36a, the guiding instrument illustrated in FIG. 14 may be used such that correct position of the screws relative to the holes 35a is reached before the screws are tightened. This because the holes 35a for the cortical screws 36a in the second attachment member 5a inside the capitate and the metacarpal bone can not be seen by the operating personnel.

After a suitable setting of the second attachment member 5a with the lockable member 34a relative to the first attachment member 4a and the locking member 33a for suitable setting of the prosthesis in the palmar-dorsal plane, the locking means 43a is inserted through the holes 41a in the shanks of the locking portion 37a of the locking member and through the long-hole 46a in the locking portion 45a of the lockable member 34a and is tightened for fixation of the lockable member to the locking member.

An alternative embodiment of the second attachment member 5a with the lockable member 34a according to the embodiment of FIGS. 7-14, is illustrated in FIGS. 16-19. Here, the second attachment member 5b with the lockable member 34b comprises an elongated and substantially plate-like member which is made in one piece, i.e. is integral with the lockable member 34b, and which is configured with holes 35b which extend transversely through said plate-like member and which are situated in line in the longitudinal direction thereof, said holes being provided for means 36b for attachment of said second attachment member to the capitate 27b of the carpus 26b and to the metacarpal bone 28a, i.e. to the outer side of said bones. In the illustrated embodiment, the second attachment member 5b has five holes 35b for attachment means 36b, of which the hole closest to the lockable member is angled relative to the other holes, because the plate-like second attachment member is made in one piece with the lockable member via an angular portion of the plate and a hole is provided in said portion. Said attachment means 36b consists of e.g. so called cortical screws. The attachment of the attachment means 36b is performed in substantially the same manner as at the embodiment of FIGS. 7-15. However, it is here possible to dispense with the instrument of FIG. 15, since the plate-like second attachment member 5b, contrary to the conically tapering second attachment member 5a according to FIGS. 7-10 and 14-15, extends outside the capitate 27b and the metacarpal bone 28b.

The other members of the wrist prosthesis 1b according to FIGS. 16-19 correspond with the wrist prosthesis of FIGS. 7-15 and the attachment is performed in a corresponding way.

The members of the wrist prosthesis 1b of FIGS. 16-19 have the same reference numerals as the corresponding members of the wrist prosthesis of FIGS. 7-15, but with the suffix "b" instead of the suffix "a".

The wrist prosthesis 1c according to FIGS. 20-24, which is somewhat modified in relation to the wrist prosthesis 1a according to FIGS. 7-15 and the wrist prosthesis 1b according to FIGS. 16-19, comprises a first prosthesis member 2c and a second prosthesis member 3c. The first prosthesis member 2c comprises a first attachment member 4c and the second prosthesis member 3c a second attachment member 5c. The first prosthesis member 2c also comprises a locking member 33c instead of a socket member 6 and the second prosthesis member 3c a lockable member 34c instead of a head member 7. The first and second attachment members 4c, 5c are in the illustrated embodiment both shaped as screws, but may be shaped otherwise.

The first and second attachment members 4c, 5c are configured with a hole 8c and 9c respectively. The hole 8c in the first attachment member 4c has at least partly a conical shape and is at least partly configured with a thread 14c, like the holes 8, 8a and 8b. The hole 9c in the second attachment member 5c has at least partly a conical shape, like the hole 9.

The locking member 33c is configured with an attachment portion 16c, e.g. an attachment pin, which is insertable into the hole 8c in said first attachment member 4c for location of the locking member therein. Accordingly, the attachment portion 16c has a conically tape-ring outer side 17c. The shape and size of the attachment portion 16c and the shape and size of the hole 8c in the first attachment member 4c are chosen such that they, when pressed together, form a press fit, such that the locking member 33c and the first attachment member 4c can be brought to attach to each other by pressing said members together.

The lockable member 34c is configured with an attachment portion 19c, e.g. an attachment pin, which is insertable into the hole 9c in said second attachment member 5c for location of the locking member therein. Accordingly, the attachment portion 19c has a conically tapering outer side 20c. The shape and size of the attachment portion 19c and the shape and size of the hole 9c in the second attachment member 5c are chosen such that they, when pressed together in an axial direction, form a press ft, such that the lock-able member 34c and the second attachment member 5c can be brought to attach to each other by pressing said members together.

The lockable member 34c is adjustably settable relative to the locking member 33c and in set position fixable to the locking member.

The locking member 33c and the lockable member 34c are, except that the lockable member in this embodiment is a separate member which is not integral with the second attachment member 5c, configured in a corresponding manner as the embodiments of FIGS. 7-15 and FIGS. 16-19.

Thus, except for the attachment portion 16c, the locking member 33c is also configured with a locking portion 37c which is connected to the attachment portion. The locking portion 37c is configured for fixation or attachment of the lockable member 34c thereto. The attachment portion 16c is configured with a hole 38c which extends through said attachment portion and in the longitudinal direction thereof for insertion therein of a partly threaded attachment means 39c for tightening or securing by screwing the locking member 33c to the first attachment member 4c by bringing said attachment means to cooperate with the threaded portion 14c of the hole 8c in said first attachment member. The locking portion 37c of the locking member 33u is in the illustrated embodiment substantially U-shaped and comprises two shanks 40c with holes 41c, 42c provided in said shanks opposite each other. Each shank 40c is in the illustrated embodiment configured with two holes 41c, 42c which extend through the shank and substantially in line in the longitudinal direction of the locking portion 37c. One hole 41c is configured for a locking means 43c (inclination screw) for fixation or attachment of the lockable member 34c to the locking member 33c and the other hole 42c is configured for an axis 44c about which the lockable member can pivot for adjustable setting thereof relative to the locking member.

Correspondingly, the lockable member 34c comprises in the illustrated embodiment a substantially flange-like lockable portion 45c for insertion between the shanks 40c of the locking portion 37c of the locking member 33c. The flange-like lockable portion 45c is configured with a curved long-hole 46c, which extends transversely therethrough, for said locking means 43c and with a hole 47c, also extending transversely through said lockable portion, for the axis 44c about which the lockable member can pivot for adjustable setting thereof relative to the locking member. At insertion of the flange-like lockable portion 45c between the shanks 40c of the locking portion 37c of the locking member 33c, portions of the long-hole 46c are brought in line with the holes 41c for the locking means 43c in said shanks for fixation or attachment of the lockable portion to the locking portion of the locking member and the hole 47c for the pivoting axis 44c is brought in line with the holes 42c for said pivoting axis in said shanks. The lockable portion 45c of the lockable member 34c may have another shape than the flange-like shape as long as it fulfils its function and permits insertion thereof between the shanks 40c of the locking portion 37c of the locking member 33c. The long-hole 46c in the lockable portion 45c of the lockable member 34c is configured with a plurality of, e.g. three fixed positions (see e.g. FIGS. 23 and 24) corresponding with different angular positions of the lockable member relative to the locking member.

The provision of the wrist prosthesis 1c is concluded after the first and second attachment members 4c, 5c have been screwed into and attached to the radius 25c and to the capitate 27c of the carpus 26c and the metacarpal bone 28c respectively, alternatively after all members of an articulated prosthesis 1 according to FIG. 1 but the first and second attachment members 4, 5 have been removed.

Thus, the locking member 33c is attached to the first attachment member 4c by inserting the attachment portion 16c of said locking member into the hole 8c in said attachment member and the locking member is tightened or secured by screwing in the hole by means of the attachment means 39c which, after it has been moved or screwed through the hole 38c in the attachment portion of the locking member, is brought to cooperate with the thread 14c in the hole 8c in said attachment member. The tightening by screwing of the attachment means 39c as described is performed by means of a screw tool of a suit-able type. The locking member 33c is by rotation thereof brought to a suitable position in order to permit a suitable setting of the prosthesis in the medial-lateral plane before the locking member is fixed by tightening of the attachment means 39c. Accordingly, the attachment means 39c has also in this embodiment two functions, namely to lock the locking member 33c axially to the first attachment member 4c and to lock the locking member to the first attachment member such that said locking member, after a suitable rotation thereof, no longer can rotate due to the friction caused by the axial pressure between the locking member and the attachment member.

The lockable member 34c is located in the second attachment member 5c by inserting the attachment portion 19c of said locking member into the hole 9c in said attachment member. After the insertion, the lockable portion 45c of the lockable member 34c is fit in bet-ween the shanks 40c of the locking portion 37c of the locking member 33c and the lock-able member is attached to the locking member by means of a screw 44c defining the pivoting axis, said screw being inserted into the holes 42c, 47c in said members.

After a suitable setting of the second attachment member 5c with the lockable member 34c relative to the first attachment member 4c and the locking member 33c for suitable setting of the prosthesis in the palmar-dorsal plane, the locking means 43c is inserted through the holes 41c in the shanks of the locking portion 37c of the locking member and through the long-hole 46c in the locking portion 45c of the lockable member 34c and is tightened for fixation of the lockable member to the locking member.

The finger joint prosthesis 1d according to FIGS. 25-28 is somewhat modified in relation to the wrist prosthesis 1c according to FIGS. 20-24, but comprises like said wrist prosthesis a first prosthesis member 2d and a second prosthesis member 3d. Even if the prosthesis in the illustrated embodiment is configured for a finger joint, the illustrated embodiment is in principal also applicable to wrist prostheses. The first prosthesis member 2d comprises a first attachment member 4d and the second prosthesis member 3d a second attachment member 5d. The first prosthesis member 2d also comprises a locking member 33d in-stead of a socket member 6 and the second prosthesis member 3d a lockable member 34d instead of a head member 7. The first and second attachment members 4d, 5d are in the illustrated embodiment both shaped as screws and also somewhat shorter since it is a finger joint prosthesis, but may be shaped otherwise for other applications, e.g. be a little bit longer as at the illustrated wrist prostheses.

The first and second attachment members 4d, 5d are each configured with a hole 8d and 9d respectively. The hole 8d in the first attachment member 4d has at least partly a conical shape and is at least partly configured with a thread 14d, like the holes 8, 8a, 8b and 8c. The hole 9d in the second attachment member 5d has at least partly a conical shape, like the hole 9 and 9c, and is partly configured with a thread 48d.

The locking member 33d is configured with an attachment portion 16d, e.g. an attachment pin, which is insertable into the hole 8d in said first attachment member 4d for location of the locking member therein. Accordingly, the attachment portion 16d has a conically tape-ring outer side 17d. The shape and size of the attachment portion 16d and the shape and size of the hole 8d in the first attachment member 4d are chosen such that they, when pressed together in an axial direction, form a press fit, such that the locking member 33d and the first attachment member 4d can be brought to attach to each other by pressing said members together.

The lockable member 34d is configured with an attachment portion 19d, e.g. an attachment pin, which is insertable into the hole 9d in said second attachment member 5d for location of the locking member therein. Accordingly, the attachment portion 19d has a conically tapering outer side 20d. The shape and size of the attachment portion 19d and the shape and size of the hole 9d in the second attachment member 5d are chosen such that they, when pressed together in an axial direction, form a press fit, such that the lock-able member 34d and the second attachment member 5d can be brought to attach to each other by pressing said members together.

The lockable member 34d is adjustably settable relative to the locking member 33d and in set position fixable to the locking member.

The locking member 33d and the lockable member 34d are in this embodiment both configured as separate members, i.e. not made in one piece with the first and second attachment members 4d, 5d respectively, and are also configured differently from the embodiments of FIGS. 7-15, 16-19 and 20-24.

Thus, except for the attachment portion 16d, the locking member 33d is configured with a locking portion 37d which is connected to the attachment portion. The locking portion 37d is configured for fixation or attachment of the lockable member 34d thereto. The attachment portion 16d is configured with a hole 38d which extends through said attachment portion and in the longitudinal direction thereof for insertion therein of a partly threaded attachment means 39d for tightening or securing by screwing the locking member 33d to the first attachment member 4d by bringing said attachment means to cooperate with the threaded portion 14d of the hole 8d in said first attachment member. The locking portion 37d of the locking member 33d is in the illustrated embodiment configured substantially as a hemisphere with radially extending furrows or grooves 49d on a base or bottom surface thereof and with a hole 50d extending perpendicular to the hole 38d and provided for a locking means 43d (inclination screw) for fixation or attachment of the lockable member 34d to the locking member 33d, said locking means defining an axis about which the lockable member can pivot for adjustable setting thereof relative to the locking member.

Correspondingly, the lockable member 34d comprises, except for the attachment portion 19d which in comparison with the locking member 33d is somewhat longer, a lockable portion 45d which is connected to the attachment portion and configured for fixation or attachment to the locking member 33d. The attachment portion 19d is configured with a hole 51d which extends through said attachment portion and in the longitudinal direction thereof for insertion therein of a partly threaded attachment means 52d for tightening or securing by screwing the lockable member 34d to the second attachment member 5d by bringing said attachment means to cooperate with the threaded portion 48d of the hole 9d in said second attachment member. The lockable portion 45d of the lockable member 34d is in the illustrated embodiment shaped substantially as a hemisphere with radially extending furrows or grooves 53d on a base or bottom surface thereof and with a hole 54d which extends perpendicular to the hole 51d and which when attaching the locking member 33d and the lockable member 34d to each other is brought in line with the hole 50d in the locking member 33d for cooperation with the locking means 43d. During assembly of the locking member 33d and the lockable member 34d, the furrows or grooves 49d, 53d on the locking portion 37d of the locking member 33d and on the lockable portion 45d of the lockable member 34d respectively, are also brought into engagement with each other for setting of different angular positions of the lockable member relative to the locking member. After assembly at the desired angular position, the members 33d, 34d are fixed to each other by means of the locking means 43d. The shape, number and arrangement of the furrows or grooves 49d, 53d may of course vary as long as they fulfil their function and permit cooperation with each other. It is however obvious that the setting possibilities vary with the number of furrows or grooves 49d, 53d on the locking member 33d and the lockable member 34d respectively.

The provision of the finger joint prosthesis 1d is concluded after the first and second attachment members 4d, 5d have been screwed into and attached to the respective bone in the finger, alternatively after all members of an articulated prosthesis except the first and second attachment members 4, 5 have been removed.

Thus, the locking member 33d is attached to the first attachment member 4d by inserting the attachment portion 16d of said locking member into the hole 8d in said attachment member and the locking member is tightened or secured by screwing in the hole by means of the attachment means 39d which, after it has been moved or screwed through the hole 38d in the attachment portion of the locking member, is brought to cooperate with the thread 14d in the hole 8d in said attachment member. The tightening by screwing of the attachment means 39d is performed by means of a screw tool of a suitable type. For wrist applications, the locking member 33d is by rotation thereof brought to a suitable position in order to permit a suitable setting of the prosthesis in the medial-lateral plane before the locking member is fixed by tightening of the attachment means 39d. Accordingly, the attachment means 39d has also here two functions, namely to lock the locking member 33d axially to the first attachment member 4d and to lock the locking member to the first attachment member such that said locking member, after a suitable rotation thereof, no longer can rotate due to the friction caused by the axial pressure between the locking member and the attachment member.

The lockable member 34d is attached to the second attachment member 5d by inserting the attachment portion 19d of said lockable member into the hole 9d in said attachment member and the lockable member is tightened or secured by screwing in the hole by means of the attachment means 52d which, after it has been moved or screwed through the hole 51d in the attachment portion of the lockable member, is brought to cooperate with the thread 48d in the hole 9d in said attachment member. The tightening by screwing of the attachment means 52d is performed by means of a screw tool of a suitable type. After insertion, the lockable portion 45d of the lockable member 34d is assembled with or attached to the locking portion 37d of the locking member 33d as described above.

After a suitable setting of the second attachment member 5d and the lockable member 34d relative to the first attachment member 4d and the locking member 33d for suitable setting of the prosthesis in the palmar-dorsal plane, the locking means 43d is inserted through the hole 50d in the locking portion 37d of the locking member and through the hole 54d in the locking portion 45d of the lockable member and is tightened for fixation of the lockable member to the locking member.

The prostheses 1a, 1b, 1c and 1d and the members forming part thereof can be manufactured of e.g. a suitable titanium alloy, such as Tl6Al4V, since this will facilitate ingrowth of bone tissue into and around the prosthesis. At the prosthesis 1b, the substantially plate-like second attachment member 5b with the lockable member 34b may consist of a suitable steel for implants.

Except that a prosthesis according to the invention has a simple construction and is easy to position, it also provides for a small incision and that only smaller parts of the respective bone have to be cut away for attachment of the first and second attachment members. By means of the first and possibly also the second attachment member, it is possible when required, also during surgery, to decide if the joint shall be replaced (artroplasty) or the joint shall be made rigid (primary artrodhesis) and it is possible to later, if required, perform an artrodhesis and thereby use parts of the prosthesis for replacement of the joint, or even by means of parts of the prosthesis for an artrodhesis see to that the joint again can be articulated. The setting possibilities of the prosthesis for artrodhesis is extensive in the medial-lateral as well as in the palmar-dorsal plane.

The invention is not limited to the embodiments described above and illustrated in the drawings, but may vary within the scope of the subsequent claims without departing from the idea and purpose of the invention. Thus, the prosthesis members may be used at other smaller joints than wrists, e.g. at finger and toe or interphalangeal joints, pollex joints and cubital joints. The design of the prosthesis members may also vary. Thus, the holes in the first and second attachment members possibly have another shape than conical shape and the socket and head members, alternatively the locking member and the lock-able member, are of course adapted thereto. The press fit may be another type of coup-ling device. Socket and head, alternatively the locking member and lockable member, may be shaped otherwise than shown. The screw tool may also be of another suitable type than a screwdriver.

The invention claimed is:
1. Wrist prosthesis for arthrodesis of a wrist joint,
wherein the prosthesis (1c) comprises two elongated prosthesis members (2c, 3c) which each is configured for attachment thereof to at least one of the bones at the wrist joint,
wherein one of the prosthesis members (2c) comprises a first screw-like attachment member (4c) which is configured attachment to at least one of the bones at the joint and the other prosthesis member (3c) comprises a second screw-like attachment member (5c) which is configured for attachment to at least one other bone at the joint, wherein said one prosthesis member (2c) comprises a locking member (33c) and said other prosthesis member (3c) a lockable member (34c), wherein the locking member (33c) is configured with an attachment portion (16c) which is insertable into a hole (8c) in said first attachment member (4c) for attachment or location of the locking member therein, wherein the lockable member (34c) is configured with an attachment portion (19c) which is insertable into a hole (9c) in said second attachment member (5c) for attachment or location of the lockable member therein, wherein the attachment portion (16c) of the locking member (33c) is configured to define a press fit with the hole (8c) in said first attachment member (4c), and wherein the attachment portion (16c) of the locking member (33c) has a conical shape, and wherein the hole (8c) in said first attachment member (4c) has a conical shape, wherein the attachment portion (19c) of the lockable member (34c) is configured to define a press fit with the hole (9c) in said second attachment member (5c), and wherein the attachment portion (19c) of the lockable member (34c) has a conical shape, and wherein the hole (9c) in said second attachment member (5c) has a conical shape, wherein the locking member (33c) is also configured with a locking portion (37c) which is connected to the attachment portion (16c) of the locking member (33c) and configured for fixation or attachment of the lockable member (34c) thereto, and wherein the attachment portion (16c) of the locking member (33c) is configured with a hole (38c) which extends through said attachment portion (16c) and in the longitudinal direction thereof for insertion therein of a partly threaded attachment means (39c) for tightening or securing by screwing the locking member (33c) to the first screw-like attachment member (4c) by bringing said attachment means (39c) to cooperate with a threaded portion (14c) of the hole (8c) in said first screw-like attachment member (4c), wherein the locking portion (37c) of the locking member (33c) is substantially U-shaped and comprises two shanks (40c) with two holes (41c, 42c) provided in each shank (40c) opposite each other and substantially in line in the longitudinal direction of the locking portion (37c), whereby one hole (41c) is configured for a locking means (43c) for fixation or attachment of the lockable member (34c) to the locking member (33c) and whereby the other hole (42c) is configured for a pivoting axis member (44c) about which the lockable member can pivot for adjustable setting thereof relative to the locking member, wherein the lockable member (34c) comprises a lockable portion (45c) which is configured for insertion between the shanks (40c) of the locking portion (37c) of the locking member (33c), wherein the lockable portion (45c) is configured with a curved long-hole (46c) that extends transversely therethrough and configured to receive said locking means (43c), and with a hole (47c) that extends transversely therethrough and configured to receive the pivoting axis member (44c) about which the lockable member (34c) can pivot for adjustable setting thereof relative to the locking member, and wherein at insertion of the lockable portion (45c) between the shanks (40c) of the locking portion (37c), portions of the curved long-hole (46c) are brought in line with the holes (41c) in said shanks (40c) of the locking portion (37c) to allow the locking means (43c) to pass through the curved long-hole (46c) and the holes (41c) for fixation or attachment of the lockable portion to the locking portion of the locking member and the hole (47c) for the pivoting axis member (44c) is brought in line with the holes (42c) for said pivoting axis member (44c) in said shanks (40c), wherein the lockable member (34c) is configured for adjustable setting thereof relative to the locking member (33c) and for fixation thereof, in set position, to the locking member, and wherein one prosthesis member (2c) is configured for attachment to the radius (25) and the other prosthesis member (3c) is configured for attachment to one of the bones (27) of the carpus (26) and a metacarpal bone (28).

2. Prosthesis according to claim 1, wherein the long-hole (46c) in the lockable portion (45c) of the lockable member (34c) is configured with a plurality of fixed positions corresponding to different angular positions of the lockable member relative to the locking member (33c).

3. Prosthesis according to claim 1, wherein the prosthesis member (2c) which is configured for attachment to the radius (25c) comprises said first attachment member (4c).

4. Prosthesis according to claim 1, wherein the prosthesis member (3c) which is configured for attachment to one of the bones (27c) of the carpus (26c) and a metacarpal bone (28c) comprises said second attachment member (5c).

* * * * *